United States Patent [19]

Bennett et al.

[11] Patent Number: 5,612,029
[45] Date of Patent: Mar. 18, 1997

[54] TISSUE PLASMINOGEN ACTIVATOR GLYCOSYLATION VARIANTS WITH IMPROVED THERAPEUTIC PROPERTIES

[75] Inventors: William F. Bennett, San Mateo; Bruce A. Keyt, Pacifica; Nicholas F. Paoni, Moraga, all of Calif.

[73] Assignee: Genentech, Inc., San Francisco, Calif.

[21] Appl. No.: 436,697

[22] Filed: May 8, 1995

Related U.S. Application Data

[62] Division of Ser. No. 389,611, Feb. 13, 1995, abandoned, which is a continuation of Ser. No. 275,462, Jul. 13, 1994, abandoned, which is a continuation of Ser. No. 894,213, Jun. 3, 1992, abandoned.

[51] Int. Cl.[6] .................. A61K 38/49; C12N 9/48; C12N 9/64
[52] U.S. Cl. .................. 424/94.64; 424/94.63; 435/212; 435/226; 435/68.1
[58] Field of Search .................. 424/94.63, 94.64; 435/172.3, 212, 219, 226, 68.1

[56] References Cited

U.S. PATENT DOCUMENTS

| | | | |
|---|---|---|---|
| 4,752,603 | 6/1988 | Collen et al. | 514/21 |
| 4,753,879 | 6/1988 | Rosa | 435/172.3 |
| 4,766,075 | 8/1988 | Goeddel et al. | 435/172.3 |
| 4,772,585 | 9/1988 | Sarnoff | 435/240.2 |
| 4,837,022 | 6/1989 | Kakimoto | 424/94.3 |
| 4,839,169 | 6/1989 | Whittle | 435/94.3 |
| 4,935,237 | 6/1990 | Higgins et al. | 424/94.64 |
| 4,960,702 | 10/1990 | Rice et al. | 435/226 |
| 4,968,617 | 11/1990 | Johnston et al. | 435/212 |
| 4,980,165 | 12/1990 | Isaacs et al. | 424/94.64 |
| 5,041,376 | 8/1991 | Gething et al. | 435/172.3 |
| 5,108,901 | 4/1992 | Anderson et al. | 435/23 |
| 5,112,609 | 5/1992 | Johnston et al. | 424/94.64 |
| 5,232,847 | 8/1993 | Edwards et al. | 435/226 |
| 5,242,688 | 9/1993 | Burck et al. | 424/94.64 |
| 5,246,850 | 9/1993 | Bennett et al. | 435/240.2 |
| 5,258,180 | 11/1993 | Gill et al. | 424/94.64 |
| 5,262,170 | 11/1993 | Anderson et al. | 424/94.64 |
| 5,270,198 | 12/1993 | Anderson et al. | 435/240.2 |
| 5,304,482 | 4/1994 | Sambrook et al. | 435/226 |
| 5,342,616 | 8/1994 | Cohen | 424/94.64 |
| 5,344,773 | 9/1994 | Wei et al. | 435/226 |
| 5,366,730 | 11/1994 | Kohnert et al. | 424/94.64 |
| 5,385,732 | 1/1995 | Anderson et al. | 424/94.64 |
| 5,409,699 | 4/1995 | Kohnert et al. | 424/94.64 |

FOREIGN PATENT DOCUMENTS

| | | |
|---|---|---|
| 71802/87 | 6/1986 | Australia . |
| 093619 | 11/1983 | European Pat. Off. . |
| 112122 | 6/1984 | European Pat. Off. . |
| 199574 | 10/1986 | European Pat. Off. . |
| 201153 | 11/1986 | European Pat. Off. . |
| 207589 | 1/1987 | European Pat. Off. . |
| 211592 | 2/1987 | European Pat. Off. . |
| 225286 | 6/1987 | European Pat. Off. . |
| 227462 | 7/1987 | European Pat. Off. . |
| 233013 | 8/1987 | European Pat. Off. . |
| 231624 | 8/1987 | European Pat. Off. . |
| 238304 | 9/1987 | European Pat. Off. . |
| 242836 | 10/1987 | European Pat. Off. . |
| 241209 | 10/1987 | European Pat. Off. . |
| 240334 | 10/1987 | European Pat. Off. . |
| 241208 | 10/1987 | European Pat. Off. . |
| 253582 | 1/1988 | European Pat. Off. . |
| 253241 | 1/1988 | European Pat. Off. . |
| 266032 | 5/1988 | European Pat. Off. . |
| 292009 | 11/1988 | European Pat. Off. . |
| 290118 | 11/1988 | European Pat. Off. . |
| 297066 | 12/1988 | European Pat. Off. . |
| 293936 | 12/1988 | European Pat. Off. . |
| 293934 | 12/1988 | European Pat. Off. . |
| 299706 | 1/1989 | European Pat. Off. . |
| 304311 | 2/1989 | European Pat. Off. . |
| 339505 | 11/1989 | European Pat. Off. . |
| 352904 | 1/1990 | European Pat. Off. . |
| 351246 | 1/1990 | European Pat. Off. . |
| 370205 | 5/1990 | European Pat. Off. . |
| 2593393 | 7/1987 | France . |
| 3537176A1 | 10/1985 | Germany . |
| WO84/01960 | 5/1984 | WIPO . |
| WO86/01538 | 3/1986 | WIPO . |
| WO87/04722 | 8/1987 | WIPO . |
| WO88/05081 | 7/1988 | WIPO . |
| WO88/10119 | 12/1988 | WIPO . |
| WO89/00191 | 1/1989 | WIPO . |
| WO89/00197 | 1/1989 | WIPO . |
| WO89/11531 | 11/1989 | WIPO . |
| WO89/12681 | 12/1989 | WIPO . |
| WO90/02798 | 3/1990 | WIPO . |
| WO90/10649 | 9/1990 | WIPO . |
| WO92/02612 | 2/1992 | WIPO . |

OTHER PUBLICATIONS

*Webster's II New Riverside University Dictionary*, ex:The Riverside Publishing Company pp. 126 (1984).

*Pharmacia Fine Chemicals Catalogue* 84 (1 and 6) (1984).

Agnelli et al., "Sustained thrombolysis with DNA–recombinant tissue type plasminogen activator in rabbits" *Blood* 66(2):399–401 (1985).

Ahern et al., "Site–directed mutagenesis in human tissue–plasminogen activator: Distinguishing sites in the amino–terminal region required for full fibrinolytic activity and rapid clearance from the circulation" *Journal of Biological Chemistry* 265(10):5540–5545 (1990).

Bennett et al., "Mapping the functional determinants of tissue plasminogen activator" *Fibrinolysis*, 10th International Congress on Fibrinolysis vol. 4(Suppl. 3):Abstr. No. 37 (1990).

(List continued on next page.)

Primary Examiner—Dian C. Jacobson
Attorney, Agent, or Firm—Ginger R. Dreger

[57] ABSTRACT

The invention concerns tissue plasminogen activator (t-PA) variants which are glycosylated at any of positions 103–105, and are devoid of functional carbohydrate structure at position 117 of wild-type human t-PA amino acid sequence. The variants have extended circulatory half-life and substantially retained fibrin binding, or improved in vivo fibrinolytic potency, as compared to wild-type human t-PA.

2 Claims, 3 Drawing Sheets

OTHER PUBLICATIONS

Bennett, W.F. et al., "High resolution analysis of functional determinants on human tissue-type plasminogen activator" *Journal of Biological Chemistry* 266:5191–5201 (1991).

Berman and Lasky, "Engineering glycoproteins for use as pharmaceuticals" *Trends in Biotechnology* 3(2):51–53 (1985).

Browne et al., "A Tissue-Type Plasminogen Activator Mutant with Prolonged Clearance In Vivo" *Journal of Biological Chemistry* 263(4):1599–1602 (1988).

Bugelski, P.J. et al., "Uptake of human recombinant tissue-type plasminogen activator by rat hepatocytes in vivo: an electron microscope autoradiographic study" *Throm. Res.* 53:287–303 (1989).

Cambier et al., "Pharmacokinetics and thrombolytic properties of a nonglycosylated mutant of human tissue-type plasminogen activator, lacking the finger and growth factor domains, in dogs with copper coil-induced coronary artery thrombosis" *J. Cardiovasc. Pharmacol.* 11:468 (1988).

Collen et al., "Pharmacokinetics and thrombolytic properties of deletion mutants of human tissue-type plasminogen activator in rabbits" *Blood* 71(1):216–219 (Jan. 1988).

Collen et al., "Thrombolytic and pharmacokinetic properties of human tissue-type plasminogen activator variants, obtained by deletion and/or duplication of structural/functional domains, in a hamster pulmonary embolism model" *Thromb. Haemost.* 65:174–180 (1991).

Eisenberg et al., "Sustained Fibrinolysis After Administration of t-PA despite its short half-life in the circulation" *Thromb. and Haemost.* 57(1):35–40 (1987).

Eisert et al., "Bolus treatment regimen of t-PA expedites rate of lysis in vivo without increasing risk of bleeding" *Haemostasis* (Abstract, 5th Congress of the Society on Thromb. and Haemost. (Feb. 1988) Frankfurt) pp. 85 (114) (1988).

Eisert et al., "Repeated bolus administration of rTPA at 30 minute intervals lyses clots as efficiently as continuous 2 hour infusion" *Blood (Supplement)* (Abstract (28th Annual Mtg of the Am. Society of Hematol. (Dec. 1986)) 68(5):1208 (1986).

Fu et al., "Disposition of a novel recombinant tissue plasminogen activator, Δ2–89 tpa, in mice" *Thrombosis Research* 50:33–41 (1988).

Gardell et al., "Isolation, Characterization, and cDNA Cloning of a Vampire Bat Salivary Plasminogen Activator" *Journal of Biological Chemistry* 264(30):17947–17952 (1989).

Gold and Leinbach, "Prevention of acute reocclusion after thrombolysis with intravenous recombinant tissue plasminogen activator" *Tissue Plasminogen Activator in Thrombolytic Therapy*, Sobel et al., New York:Dekker vol. Chapter 7:115–130 (1987).

Gold et al., "Rapid and sustained coronary artery recanalization with combined bolus injection of recombinant tissue-type plasminogen activator and monoclonal antiplatelet GPIIb/IIIa antibody in a canine preparation" *Circulation* 77(3):670–677 (1988).

Gunzler, W. et al., "The Primary Structure of High Molecular Mass Urokinas from Human Urine The Complete Amino Acid Sequence of the A Chain," *Hoppe–Seyler's Z. Physiol. Chem. Bd.* 363:S. 1155–1165 (1982).

Haigwood et al., "Variants of human tissue-type plasminogen activator substituted at the protease cleavage site and glycosylation sites, and truncated at the N-and C-termini" *Prot. Engineering* 2:611–620 (1989).

Harris, "Second Generation Plasminogen Activators" *Protein Engineering* 1(6):449–458 (1987).

Higgins and Bennett, "Tissue plasminogen activator: the biochemistry and pharmacology of variants produced by mutagenesis" *Ann. Rev. Pharmacol. Toxicol.* 30:91–121 (1990).

Holmes, W. et al., "Cloning and Expression of the Gene for Pro–Urokinase in *Escherichia Coli*," *Bio/Technology* 3:923–929 (1985).

Hotchkiss A. et al., "The influence of carbohydrate structure on the clearance of recombinant tissue-type plasminogen activator" *Thrombosis and Haemostasis* 60(2):255–261 (1988).

Hotchkiss et al., "The activity of a single chain rt–PA mutant in a primates and rabbits" *Thromb. Haemost.* (Abstract only) 58:491 (1987).

Huber and Bode, "Structural Basis of the Activation and Action of Trypsin" *Accounts of Chemical Research* 11;114–122 (1978).

Johannessen et al., "Fibrin affinity and clearance of t–PA deletion and substitution analogues" *Thromb. Haemost.* 63:54–59 (1990).

Kalyan et al., "Structure–function analysis with tissue-type plasminogen activator" *Journal of Biological Chemistry* 263:3971–3978 (1988).

Kasai, S. et al., "Proteolytic Cleavage of Single–chain Pro–urokinase Induces Conformational Change which Follows Activation of the Zymogen and Reduction of Its High Affinity for Fibrin," *Journal of Biological Chemistry* 260(22):12377–12381 (1985).

Kasai, S. et al., "Thrombolytic Properties of an Inactive Proenzyme Form of Human Urokinase Secreted from Human Kidney Cells," *Cell Structure and Function* 10:151–159 (1985).

Kassell et al., "Zymogens of Proteolytic Enzymes" *Science* 180:1022–1027 (1973).

Kaufman et al., "Expression and Amplification of DNA Introduced into Mammalian Cells" *Gene Amplification*, Cold Spring Harbor Laboratory pp. 245–250 (1982).

Keyt et al., "Slowly clearing mutants of tissue plasminogen activator with conserved fibrinolytic activity" *Fibrinolysis*, Amsterdam:11th International Congress on Fibrinolysis vol. 6(Suppl. 2):Abstr. No. 64 (1992).

Khan et al., "Effectiveness of multiple bolus administration of tissue-type plasminogen activator in acute myocardial infarction" *Am. J. Cardiol.* 65:1051–1056 (1990).

Ladenheim, R.G. et al., "N–Linked Glycosylation Affects the Processing of Mouse Submaxillary Gland Prorenin in Transfected AtT20 Cells" *European Journal of Biochemistry* 198(2):535–540 (1991).

Larsen et al., "Pharmacokinetic and distribution analysis of variant forms of tissue-type plasminogen activator with prolonged clearance in rat" *Blood* 73:1842–1850 (1989).

Lau et al., "A modified human tissue plasminogen activator with extended half–life in vivo" *Bio/Technology* 5:953–958 (1987).

Lau et al., "A modified human tissue plasminogen activator with extended half–life in vivo" *Bio/Technology* 6:734 (1988).

Lijnen and Collen, "Strategies for the improvement of thrombolytic agents" *Thromb. Haemostas.* 66(1):88–110 (1991).

Lijnen et al., "Effect of fibrin-like stimulators on the activation of plasminogen by tissue-type plasminogen activator (t-PA)—studies with active site mutagenized plasminogen and plasmin resistant t-PA" *Thromb. Haemost.* 64:61–68 (1990).

Machamer and Rose, "Influence of New Glycosylation Sites on Expression of the Vesicular Stomatitis Virus G Protein at the Plasma Membrane" *Journal of Biological Chemistry* 263(12):5948–5954 (1988).

Machamer and Rose, "Vesicular Stomatitis Virus G Proteins with Altered Glycosylation Sites Display Temperature-Sensitive Intracellular Transport and Are Subject to Aberrant Intermolecular Disulfide Bonding" *Journal of Biological Chemistry* 263(12):5955–5960 (1988).

Madison et al., "Amino acid residues that affect interaction of tissue–type plasminogen activator with plasminogen activator inhibitor 1" *Proc. Natl. Acad. Sci. USA* 87:3530–33 (1990).

Madison et al., "Serpin-Resistant Mutants of Human Tissue-Type Plasminogen Activator" *Nature* 339:721–724 (1989).

Martin et al., "Thrombolytic potency of an *E. coli*–produced novel variant of rt-PA in dogs" *Fibrinolysis* 4(Suppl. 3):Abstr. No. 26 (1990).

Morton, P.A. et al., "Catabolism of tissue–type plasminogen activator by the human hepatoma cell line Hep G2" *Journal of Biological Chemistry* 264:7228–7235 (1989).

Neuhaus, "Improved thrombolysis with a modified dose regimen of recombinant tissue–type plasminogen activator" *JACC* 14:1566–1569 (1989).

Nilsson, S. et al., "Turnover of tissue plasminogen activator in normal and hepatectomized rabbits" *Thrombosis Research* 39:511–521 (1985).

Ny et al., "Cloning and Characterization of a cDNA for Rat Tissue-Type Plasminogen Activator" *DNA* 7(10):671–677 (1988).

Pannekoek et al., "Mutants of human tissue–type plasminogen activator (t-PA): structural aspects and functional properties" *Fibrinolysis* 2;123–132 (1988).

Parekh, Raj B. et al., "Cell-Type-Specific and Site-Specific N-Glycosylation of Type I and Type II Human Tissue Plasminogen Activator" *Biochemistry* 28:7644–7662 (1989).

Pennica et al., "Cloning and Expression of Human Tissue-type Plasminogen Activator cDNA in *E. coli*," *Nature* 301:214–221 (1983).

Petersen et al., "The effect of polymerised fibrin on the catalytic activities of one-chain tissue–type plasminogen activator as revealed by an analogue resistant to plasmin cleavage" *Biochemica Et Biophysica Acta* 952:245–254 (1988).

Purvis, J.A. et al., "Effectiveness of double bolus alteplase in the treatment of acute myocardial infarction" *Am. J. Cardiology* 68:1570–1574 (1991).

Refino et al., "The pharmacokinetics and circulatory metabolism of a long half life mutant of rt-PA" *Fibrinolysis* 2:30 (1988).

Rickles et al., "Molecular Cloning of Complementary DNA to Mouse Tissue Plasminogen Activator mRNA and Its Expression During F9 Teratocarcinoma Cell Differentiation" *Journal of Biological Chemistry* 263(3):1563–1569 (1988).

Rijken and Collen, "Purification and Characterization of the Plasminogen Activator Secreted by Human Melanoma Cells in Culture," *Journal of Biological Chemistry* 256(13):7035–7041 (1981).

Rijken et al., "Fibrinolytic Properties of One-chain and Two-chain Human Extrinsic (Tissue-type) Plasminogen Activator" *Journal of Biological Chemistry* 257:2920–2925 (1982).

Ringe, D., "The sheep in Wolf's clothing" *Nature* 339:658–659 (1989).

Ross et al., "Plasminogen Activators" *Annual Reports in Medicinal Chemistry*, Chapter 12, 23:111–120 (1988).

Sobel et al., "Augmented and sustained plasma concentrations after intramuscular injections of molecular variants and deglycosylated forms of tissue–type plasminogen activators" *Circulation* 81:1362–1373 (1990).

Sobel et al., "Improvement of regional myocardial metabolism after coronary thrombolysis induced with tisse–type plasminogen activator or streptokinase" *Circulation* 69:983–990 (1984).

Spellman et al., "Carbohydrate structures of human tissue plasminogen activator expressed in chinese hamster ovary cells" *Journal of Biological Chemistry* 264(24):14100–14111 (1989).

Steffens, G. et al., "The Complete Amino Acid Sequence of Low Molecular Mass Urokinas from Human Urine" *Hoppe–Seyler's Z. Physiol. Chem. Bd.* 363:S. 1043–1058 (1982).

Tate et al., "Functional role of proteolytic cleavage at arginine–275 of human tissue plasminogen activator as assessed by site-directed mutagenesis" *Biochemistry* 26:338–343 (1987).

Topol, E.J., "Ultrathrombolysis" *J. Am. Coll. Cardiol.* 15:922–924 (1990).

Trill et al., "Expression and characterisation of finger protease (FP); a mutant tissue–type plasminogen activator (t–PA) with improved pharmacokinetics" *Fibrinolysis* 4:131–140 (1990).

van Zonneveld et al., "On the relation between structure and function of human tissue–type plasminogen activator" *Thrombos. Haemostas.* 54(1):4 (1985).

van Zonneveld, A.J. et al., "Autonomous functions of structural domains on human tissue–type plasminogen activator" *Proc. Natl. Acad. Sci. USA* 83:4670–4677 (1986).

Vaughan, D.E. et al., "Recombinant plasminogen activator inhibitor–1 reverses the bleeding tendency associated with the combined administration of tissue–type plasminogen activator and aspirin in rabbits" *J. Clin. Invest.* 84:586–591 (1989).

Vehar, G.A. et al., "Characterization Studies of Human Tissue Plasminogen Activator Produced by Recombinant DNA Technology" *Cold Spring Harbor Symposia on Quantitative Biology* LI:551–562 (1986).

Verheijen, J.H. et al., "Involvement of finger domain and kringle 2 domain of tissue–type plasminogen activator in fibrin binding and stimulation of activity by fibrin" *EMBO Journal* 5:3525–3530 (1986).

Verstraete et al., "Bolus Alteplase" *Lancet* 14;1566–1569 (1989).

Wiman, B. et al., "Inactivation of tissue plasminogen activator in plasma" *Journal of Biological Chemistry* 259:3644–3647 (1984).

Collen, D. et al., "Comparative thrombolytic properties of tissue–type plasminogen activator and of a plasminogen activator inhibitor –1–resistant glycosylation variant, in a combined arterial and venous thrombosis model in the dog" *Thrombosis and Haemostasis* 72(1):98–104 (1994).

Keyt, B. et al., "A faster-acting and more potent form of tissue plasminogen activator" *Proc. Natl. Acad. Aci. USA* 91:3670–3674 (1994).

Krishnamurti, C. et al., "PAI-1—Resistant t-PA: Low doses prevent fibrin deposition in rabbits with increased PAI-1 activity" *Blood* 87(1):14–19 (1996).

Paoni, N. et al., "A slow clearing, fibrin-specific, PAI-1 resistant variant of t-PA (T103N, KHRR 296–299 AAAA)" *Thrombosis and Haemostasis* 70(2):307–312 (1993).

Dorr et al., "Prevention of postoperative adhesions by tissue-type plasminogen activator (t-PA) in the rabbit" *Eur. J. Obstet. Gynecol. Reprod. Biol. (Netherlands)* 37(8):287–91 (1990).

Menzies and Ellis, "Intra-abdominal adhesions and their prevention by topical tissue plasminogen activator" *J R Soc Med* 82(9):534–5 (1989).

Mordenti, J. and W. Chappell, "The Use of interspecies scaling in toxicokinetics" *Toxicokinetics and New Drug Development*, Yacobi, Skelly and Batra, eds., New York:Pergamon Press pp. 42–49 (1989).

Orita et al., "Inhibition of postsurgical adhesions in a standardized rabbit model: intraperitoneal treatment with tissue plasminogen activator" *Int. J. Fertil.* 36(3):172–7 (1991).

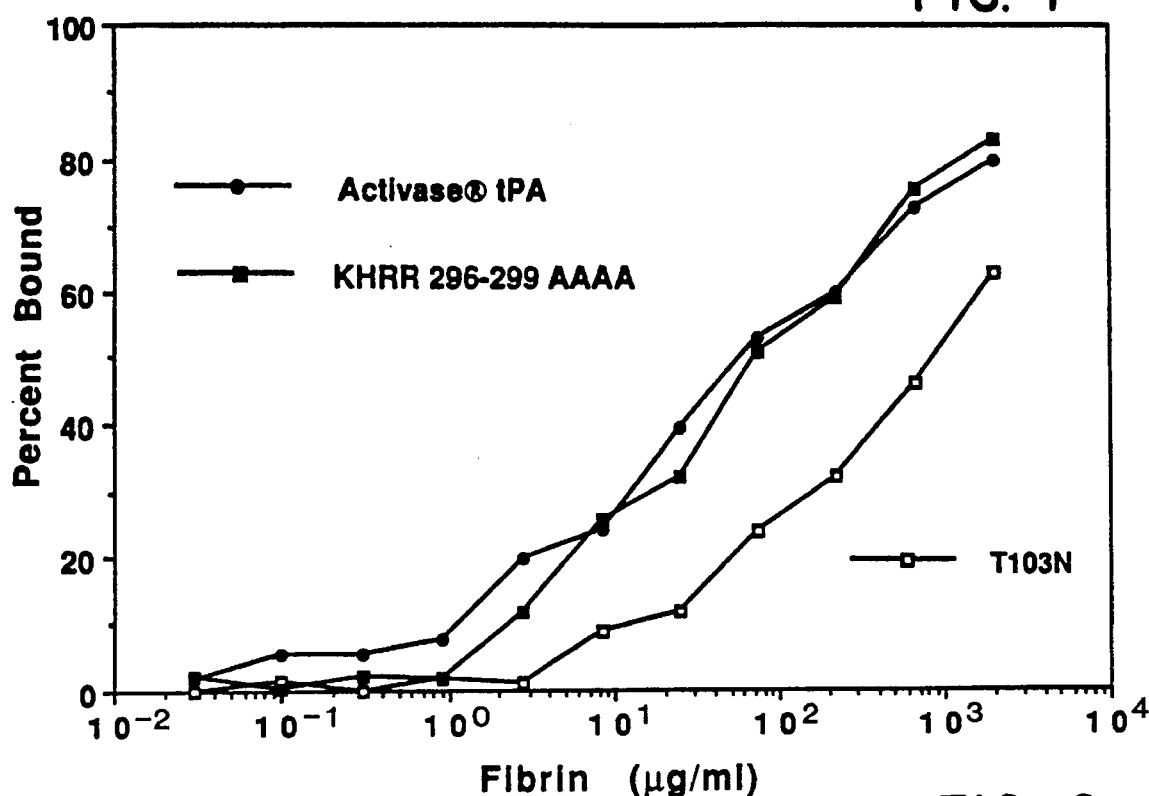
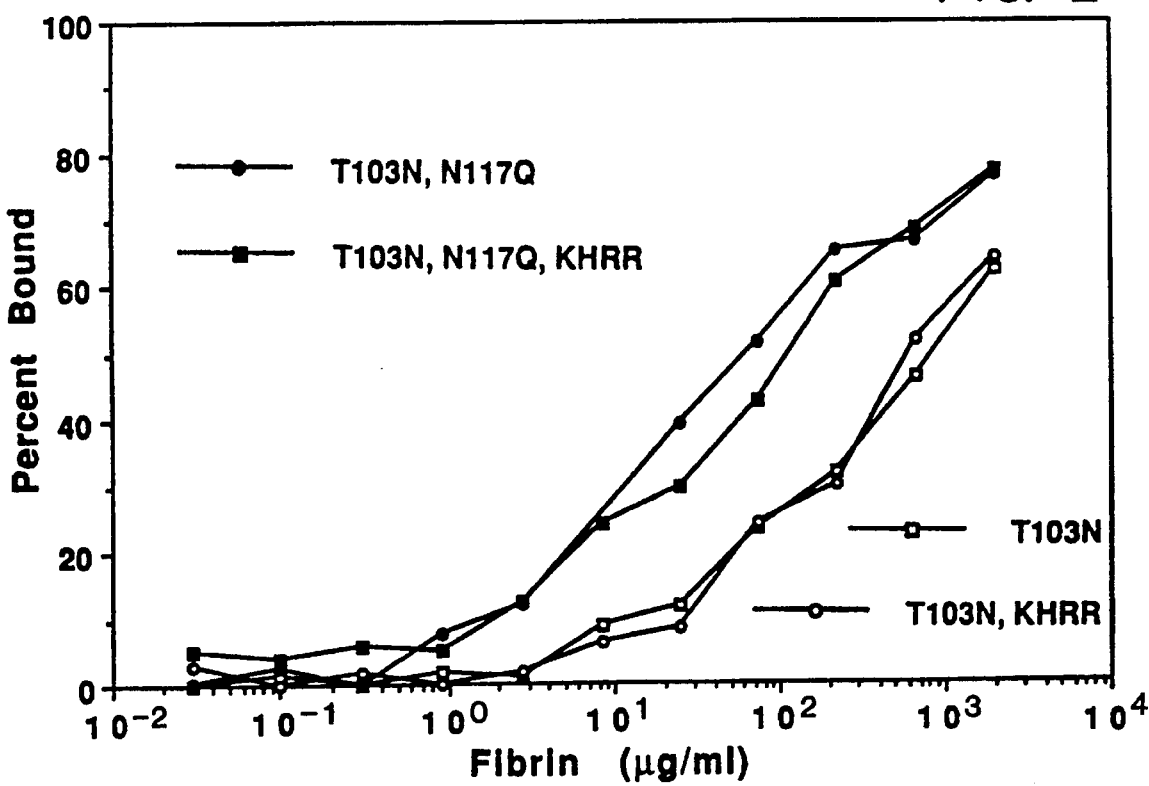

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:1:

TGTGCTCCAA TTGCCCCTGT AGCT  24

( 2 ) INFORMATION FOR SEQ ID NO:2:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:2:

GCCACTCTCG GATGTATTCC ACGTGCCCCT            30

( 2 ) INFORMATION FOR SEQ ID NO:3:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:3:

CGCGCTGCTT TGCCAGTTGG TGCA            24

( 2 ) INFORMATION FOR SEQ ID NO:4:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:4:

CCGCTCTCCG GGCGACGCCG CGGCCGCGGC AAAGAT            36

TISSUE PLASMINOGEN ACTIVATOR GLYCOSYLATION VARIANTS WITH IMPROVED THERAPEUTIC PROPERTIES

This is a divisional of applications Ser. No. 08/389,611 filed on 13 Feb. 1995, now abandoned, which is a continuation of application Ser. No. 08/275,462 filed on 13 Jul. 1994, now abandoned, which is a continuation of application Ser. No 07/894,213 filed on 03 Jun. 1992, now abandoned, which application is incorporated herein by reference and to which application priority is claimed under 35 USC §120.

BACKGROUND OF THE INVENTION

I. Field of the Invention

This invention is directed to tissue plasminogen activator (t-PA) variants having extended circulatory half-life as compared to wild-type human t-PA while substantially retaining its fibrin binding affinity. Certain variants additionally exhibit improved in vivo fibrinolytic potency. The invention also concerns methods and means for preparing these variants, and pharmaceutical compositions comprising them.

II. Description of Background and Related Art

Tissue plasminogen activator (t-PA) is a multidomain serine protease whose physiological role is to convert plasminogen to plasmin, and thus to initiate or accelerate the process of fibrinolysis.

Initial clinical interest in t-PA was raised because of its relatively high activity in the presence, as compared to the absence, of fibrin. Wild-type t-PA is a poor enzyme in the absence of fibrin, but the presence of fibrin strikingly enhances its ability to activate plasminogen. Without stimulation, the catalytic efficiency (catalytic rate constant ($k_{cat}$)/Michaelis constant ($K_m$)) of melanoma or recombinant human t-PA (Activase® t-PA) for the activation of plasminogen is approximately 1 $nM^{-1}sec^{-1}$, whereas in the presence of fibrin or fibrin degradation products, this efficiency (pseudo-rate constant) is increased by several hundred-fold. This unusual biochemical property of t-PA is thought to translate clinically into a thrombolytic product that is less likely than non-fibrin-specific thrombolytics (such as streptokinase or urokinase) to induce systemic plasminogen activation [Sobel, B. E. et al., *Circulation* 69, 983–990 (1984)]. Recombinant human t-PA is used therapeutically as a fibrinolytic agent in the treatment of acute myocardial infarction and pulmonary embolism, both conditions usually resulting from an obstruction of a blood vessel by a fibrin-containing thrombus.

In addition to its striking fibrin specificity, t-PA exhibits several further distinguishing characteristics:

(a) T-PA differs from most serine proteases in that the single chain form of the molecule has appreciable enzymatic activity. Toward some small substrates, and toward plasminogen in the absence of fibrin, two chain t-PA has greater activity than one chain. In the presence of fibrin, however, the two forms of t-PA are equally active [Rijken et al., *J. Biol. Chem.* 257, 2920–5 (1982); Lijnen et al., *Thromb. Haemost.* 64, 61–8 (1990); Bennett et al., *J. Biol. Chem.* 266, 5191–5201 (1991)]. Most other serine proteases exist as zymogens and require proteolytic cleavage to a two-chain form to release full enzymatic activity.

(b) The action of t-PA in vivo and in vitro can be inhibited by a serpin, PAI-1 [Vaughan, D. E. et al., *J. Clin. Invest* 84, 586–591 (1989); Wiman, B. et al., *J. Biol. Chem.* 259, 3644–3647 (1984)].

(c) T-PA binds to fibrin in vitro with a $K_d$ in the μM range.

(d) T-PA has a rapid in vivo clearance that is mediated by one or more receptors in the liver [Nilsson, S. et al., *Thromb. Res.* 39, 511–521 (1985); Bugelski, P. J. et al., *Throm. Res.* 53, 287–303 (1989); Morton, P. A. et al., *J. Biol. Chem.* 264, 7228–7235 (1989)].

A substantially pure form of t-PA was first produced from a natural source and tested for in vivo activity by Collen et al., U.S. Pat. No. 4,752,603 issued 21 Jun. 1988 (see also Rijken et al., *J. Biol. Chem.*, 256:7035 [1981]). Pennica et al. (*Nature*, 301:214 [1983]) determined the DNA sequence of t-PA and deduced the amino acid sequence from this DNA sequence (see U.S. Pat. No. 4,766,075 issued 23 Aug. 1988).

Human wild-type t-PA has potential N-linked glycosylation sites at amino acid positions 117, 184, 218, and 448. Recombinant human t-PA (Activase® t-PA) produced by expression in CHO cells was reported to contain approximately 7% by weight of carbohydrate, consisting of a high-mannose oligosaccharide at position 117, and complex oligosaccharides at Asn-184 and Asn-448 [Vehar, G. A. et al., "Characterization Studies of Human Tissue Plasminogen Activator produced by Recombinant DNA Technology" Cold Spring Harbor Symposia on Quantitative Biology 1986; LI:551–562]. Position 218 has not been found to be glycosylated in native t-PA. Sites 117 and 448 appear to always be glycosylated, while site 184 is thought to be glycosylated in about fifty percent of the molecules. The t-PA molecules that are glycosylated at position 184 are termed Type II t-PA. and the molecules that are not glycosylated at position 184 are termed Type II t-PA. The most comprehensive analysis of the carbohydrate structures of CHO cell-derived human t-PA was carried out by Spellman et al., *J. Biol. Chem.* 264(24) 14100–14111 (1989), who showed that at least 17 different Asn-linked carbohydrate structures could be detected on the protein. These ranged from the high-mannose structures at position 117 to di-, tri- and tetra-antennary N-acetyllactosamine-type structures at positions 184 and 448. Type I and Type II t-PAs were reported to be N-glycosylated in an identical way at Asn-117 and Asn-448 positions, when isolated from the same cell line. For further details see also Parekh, Raj B. et al., *Biochemistry* 28, 7644–7662 (1989).

Analysis of the sequence of t-PA has identified the molecule as having five domains. Each domain has been defined with reference to homologous structural or functional regions in other proteins such as trypsin, chymotrypsin, plasminogen, prothrombin, fibronectin, and epidermal growth factor (EGF). These domains have been designated, starting at the N-terminus of the amino acid sequence of t-PA, as the finger (F) domain from amino acid 1 to about amino acid 44, the growth factor (G) domain from about amino acid 45 to about amino acid 91 (based on homology with EGF), the kringle-1 (K1) domain from about amino acid 92 to about amino acid 173, the kringle-2 (K2) domain from about amino acid 180 to about amino acid 261, and the serine protease (P) domain from about amino acid 264 to the carboxyl terminus at amino acid 527. These domains are situated essentially adjacent to each other, and are connected by short "linker" regions. These linker regions bring the total number of amino acids of the mature polypeptide to 527, although three additional residues (Gly-Ala-Arg) are occasionally found at the amino terminus. This additional tripeptide is generally thought to be the result of incomplete precursor processing, and it is not known to impart functionality. Native t-PA can be cleaved between position 275 and position 276 (located in the serine protease domain) to generate the 2-chain form of the molecule.

Each domain contributes in a different way to the overall biologically significant properties of the t-PA molecule. Domain deletion studies show that the loss of the finger, growth factor, or kringle-2 domains results in a lower affinity binding of the variant t-PA to fibrin [van Zonneveld, A. J. et al., *Proc. Natl. Acad. Sci. USA* 83, 4670–4677 (1986); Verheijen, J. H. et al., *EMBO J.* 5, 3525–30 (1986)], however, more recent results obtained with substitution mutants indicate that the kringle-2 domain is less involved in fibrin binding than earlier expected [Bennett, W. F. et al., *J. Biol. Chem.* 266 5191–5201 (1991)]. The domain deletion studies have implicated the finger and growth factor domains in clearance by the liver [Collen et al., *Blood* 71, 216–219 (1988); Kalyan et al., *J. Biol. Chem.* 263, 3971–3978 (1988); Fu et al., *Thromb. es.* 50, 33–41 (1988); Refino et al., *Fibrinolysis* 2,30 (1988); Larsen et al., *Blood* 73 1842–1850 (1989); Browne et al., *J. Biol. Chem.* 263, 1599–1602 (1988)]. The kringle-2 domain is responsible for binding to lysine. The serine protease domain is responsible for the enzymatic activity of t-PA and contains specific regions where mutations were shown to affect both fibrin binding and fibrin specificity (possibly direct interactions with fibrin), and other regions where only fibrin specificity is altered (possibly indirect interactions with fibrin) (Bennett et al., 1991,Supra). Studies with mutants resulting from site-directed alterations indicate the involvement of the glycosylation of t-PA in clearance [Lau et al., *Bio/Technology* 5, 953–958 (1987); Lau et al., *Bio/Technology* 6, 734 (1988)].

The relatively rapid clearance of wild-type human t-PA from the plasma, while it is an advantage in patients needing emergency intervention after thrombolysis, requires continuous intravenous administration to maintain therapeutic levels of t-PA in blood. The recommended total dose of Activase® t-PA for thrombolytic therapy in acute pulmonary embolism in adult patients is 100 mg given as a continuous intravenous infusion over 2 hours. T-PA derivatives with longer plasma half-life (slower clearance) could be administered as a bolus injection and would yield higher plasma concentrations than can be obtained with continuous infusion of wild-type t-PA, which may result in the reduction of the effective dose. Slower clearing t-PA mutants would offer particular advantages in the treatment of conditions such as deep vein thrombosis, treatment following reperfusion of an infarct victim, treatment of pulmonary embolism, or treatment of peripheral arterial thrombosis (peripheral vascular disease).

The need for t-PA variants that can be administered in a bolus form is underlined by recent interest in bolus administration of wild-type human t-PA (especially in single chain form) with the aim of promoting early infarct-related coronary artery patency and improving myocardial salvage [Verstraete et al., *Lancet* 14, 1566–1569 (1989) ; Neuhaus, *JACC* 14, 1566–1569 (1989) ; Khan et al., *Am. J. Cardiol.* 65, 1051–1056 (1990) ; Purvis, J. A. et al. *Am. J. Cardiology* 68, 1570–1574 (1991)]. Results of recent clinical studies indicate that bolus intravenous administration of wild-type human t-PA not only hastens the initiation of thrombolytic therapy but the rapid achievement of a relatively high t-PA concentration also enhances thrombolysis [Neuhaus, K. L., Supra, Topol, E. J., *J. Am. Coll. Cardiol.* 15, 922–924 (1990)].

T-PA variants with decreased clearance have been prepared by deleting individual amino acids, partial domains, or complete domains from the molecule. The following publications are representative of attempts to reduce the clearance rate of wild-type t-PA by deletion of part or all of the growth factor and/or finger domains, optionally combined with other mutations: Browne et al., 1988, Supra; Johannessen et al., *Thromb. Haemostas*, 63, 54–59 (1990); Collen et al., 1988, Supra; Kalyan et al., 1988, Supra; Sobel et al., *Circulation* 81, 1362–73 (1990); Cambier et al. *J. Cardiovasc. Pharmacol.*, 11:468 (1988); *Ann. Rev. Pharmacol. Toxicol.*, 30:91 (1990); Trill et al., *Fibrinolysis* 4, 131–140 (1990); U.S. Pat. No. 4,935,237 (issued 19 Jun. 1990); EP-A 241,208 (published 14 Oct. 1987); EP-A 240,334 (published 7 Oct. 1987). A t-PA variant with a duplicated kringle-2 domain, and reportedly reduced plasma clearance, was disclosed by Collen et al., *Thromb. Haemost.* 65, 174–180 (1991).

A variety of amino acid substitution t-PA variants have been evaluated for their ability to decrease the clearance rate and/or increase the half-life of t-PA. Substitutions in the amino acid regions 63–72 (and especially at positions 67 and 68), and 42–49 have been reported to increase the plasma half-life of wild-type human t-PA [see WO 89/12681, published 28 Dec. 1989 and Ahern et al., *J. Biol. Chem.* 265, 5540 (1990)]. The substitution of arginine at position 275 of native, mature t-PA with glutamic acid has been described to have a clearance rate about two times slower than that of wild-type human t-PA [Hotchkiss et al., *Thromb. Haemost.*, 58:491 (1987)].

Another approach to decrease the clearance rate and/or extend the half-life of t-PA has been to complex the t-PA molecule with a second molecule. For example, a t-PA-polyethylene-glycol conjugate has been reported to reduce the rate of clearance of t-PA, as reported in EP-A 304,311 (published 22 Feb. 1989). A monoclonal antibody to t-PA has been reported to increase the functional half-life of t-PA in vivo without decreasing its activity (see EP-A 339,505 published 2 Nov. 1989).

The involvement of carbohydrates in the clearance of t-PA has also been studied. T-PA variants with different carbohydrate profile from that of wild-type human t-PA have been made and tested.

As examples of this approach, one or more of positions 60, 64, 65, 66, 67, 78, 79, 80, 81, 82, 103, 105, 107, and 250 have been substituted with appropriate amino acids to create molecules with glycosylation sites at or near some of these residues (see WO 89/11531, published 30 Nov. 1989 and U.S. Ser. No. 07/480691, filed 15 Feb. 1990, now abandoned, and its continuation U.S. Pat. No. 5,270,198 filed 21 Jan. 1992). Of these t-PA variants, the T103N extra-glycosylation t-PA mutant, for example, had about five fold slower clearance than native t-PA.

Other work focused on converting the glycosylation sites of wild-type t-PA to non-glycosylated sites. An unglycosylated variant of t-PA consisting of the kringle-2 and protease domains was described to have a slower plasma clearance than wild-type t-PA [Martin et al., *Fibrinolysis* 4 (Suppl. 3):9 (Abstract 26) (1990)]. Hotchkiss et al. [*Thromb. Haemost.*, 60:255 (1988)] selectively removed oligosaccharide residues from the t-PA molecule, and demonstrated that the removal of these residues decreased the rate of clearance of t-PA. These researchers, and Lau et al. [(1987), Supra; (1988), Supra] also generated the t-PA variant N117Q (wherein asparagine at position 117 of wild-type human t-PA was substituted with glutamine) to prevent glycosylation at position 117. This variant, similarly to that obtained by enzymatic removal of the high mannose oligosaccharide at this position, exhibited an about two fold slower clearance rate than wild-type human t-PA. See also EP-A 238,304 published 23 Sep. 1987 and EP-A 227,462 published 1 Jul. 1987.

Further human t-PA glycosylation variants were described and reported to have reduced clearance rates in the following publications: Ahern et al., Supra (Q42N, H44E, N117Q t-PA); Collen et al., (1988), Supra [del(C6-I86)N117Q t-PA, and del (C6-I86)N117Q,N184Q,N448Q t-PA]; Haigwood et al., *Prot. Engineer.* 2, 611 (1989) (N117Q,N184Q t-PA).

We have found that the extension of circulating half-life of wild-type human t-PA by the addition of extra glycosylation at amino acid positions 103–105 was also accompanied by a loss in fibrin binding affinity and/or plasma clot lysis activity. For example, the replacement of threonine by asparagine at amino acid position 103 of wild-type human t-PA reduced the clearance rate about five fold, but also led to a loss in t-PA function in that the fibrin binding affinity and activity of t-PA were significantly reduced. As a result, although due to its lower clearance rate the plasma concentrations of this glycosylation variant were about 4–5 fold greater than for an equivalent dose of Activase® t-PA, because of its reduced activity, the improvement made in efficacy or in vivo fibrinolytic potency was little.

The present invention is based, among other things, upon specific successful research demonstrating that a loss in t-PA fibrin binding resulting from an alteration whose primary function is to improve the pharmacokinetic properties (reduce plasma clearance, extend circulatory half-life) of wild-type t-PA can be restored with an additional alteration without compromising the slower clearance rate or extended circulatory half-life achieved. The present invention is further based on experimental proof demonstrating that the in vivo clot lysis (fibrinolytic) potency of such t-PA variants can be significantly improved over that of wild-type human t-PA, in particular if the changes in the glycosylation pattern of t-PA are accompanied by additional specific alterations in the t-PA protease domain. The results are molecules with improved fibrinolytic potency with respect to wild-type t-PA, which are also capable of a more rapid lysis of plasma clots than wild-type t-PA and may additionally have improved fibrin-specificity.

SUMMARY OF THE INVENTION

We have surprisingly found that the loss in fibrin binding observed for slow-clearing t-PA variants having an extra glycosylation site at amino acid positions 103 to 105 of wild-type human t-PA can be recovered by removing the functional carbohydrate structure at amino acid position 117. These alterations, when combined, permit the extension of circulatory half-life without compromising the fibrin binding affinity of the t-PA variant. The in vivo fibrinolytic potency (clot lysis per unit dose) of wild-type t-PA can also be improved, especially when an additional alteration improving fibrin specificity is introduced in the molecule.

Accordingly, the invention relates to t-PA variants that are glycosylated at any of positions 103–105 and are devoid of functional carbohydrate structure at position 117 of wild-type human t-PA amino acid sequence, and a) exhibit extended circulatory half-life while substantially retaining the fibrin binding affinity of wild-type human t-PA, or b) have improved in vivo fibrinolytic potency as compared to wild-type human t-PA.

In a preferred embodiment, such t-PA variants exhibit at least similar fibrin binding as compared to wild-type human t-PA.

In another preferred embodiment, such t-PA variants have increased in vivo fibrinolytic potency compared to wild-type human t-PA.

Apart from the carbohydrate at amino acid residue 117 of the native t-PA molecule, the t-PA variants of the present invention preferably retain the functional carbohydrate structure at positions glycosylated in wild-type human t-PA.

The extra glycosylation site preferably is at amino acid position 103 or 105 of wild-type human t-PA.

In one preferred embodiment, the extra glycosylation is N-linked, and the resultant variants contain an asparagine at any of amino acid positions 103–105 as part of an Asn-X-Ser or Asn-X-Thr tripeptidyl sequence, wherein X is any amino acid except proline, which prevents glycosylation.

In another preferred embodiment, the N-linked extra glycosylation site is at amino acid positions 103 or 105 of wild-type human t-PA.

In a further preferred embodiment, removal of the functional carbohydrate structure at amino acid 117 is accomplished by site-directed mutagenesis of the underlying DNA of the glycosylation signal Asn-X-Ser/Thr (where X is as hereinabove defined). In the resultant t-PA variants asparagine at position 117 of the wild-type t-PA amino acid sequence is replaced by another amino acid, which preferably is glutamine.

In a still further embodiment, the variants of the present invention have improved fibrin specificity as compared to wild-type human t-PA.

Fibrin specificity may, for example, be improved by introducing an additional alteration within the amino acid region 296–302 or 274–277 of the wild-type human t-PA amino acid sequence. The alteration preferably is the substitution of alanine for each of the amino acids at positions 296–299, or the replacement of the amino acids present at positions 274–277 of the wild-type t-PA (phenylalanine, arginine, isoleucine, lysine) by leucine, histidine, serine and threonine, respectively.

In other embodiments, the invention relates to DNA sequences encoding the variants described above, replicable expression vectors capable of expressing such DNA sequences in a transformed host cell, transformed host cells, and a process comprising culturing the host cells so as to express the DNAs encoding the t-PA variants.

In yet another embodiment, the invention relates to a composition for treating a vascular condition or disease comprising a therapeutically effective amount of the t-PA variants in admixture with a pharmaceutically acceptable carrier.

In still another embodiment, the invention provides a method of treating a vascular disease or condition in a mammal comprising administering an effective amount of the t-PA variants to the mammal.

In a further aspect, the invention relates to a method for substantially recovering the loss in fibrin binding affinity caused by the addition of an extra glycosylation at any of positions 103–105 of the wild-type human t-PA sequence, by additionally removing the functional carbohydrate structure at amino acid position 117.

BRIEF DESCRIPTION OF THE DRAWINGS

FIGS. 1 and 2 show the effect of the mutations of the present invention on the fibrin binding of the resultant t-PA variants. The loss of fibrin binding due to an extra glycosylation at amino acid position 103 of wild-type human t-PA could be recovered by the removal of the carbohydrate structure at position 117 of the wild-type human t-PA molecule.

DETAILED DESCRIPTION OF THE INVENTION

I. DEFINITIONS

Figure 3:
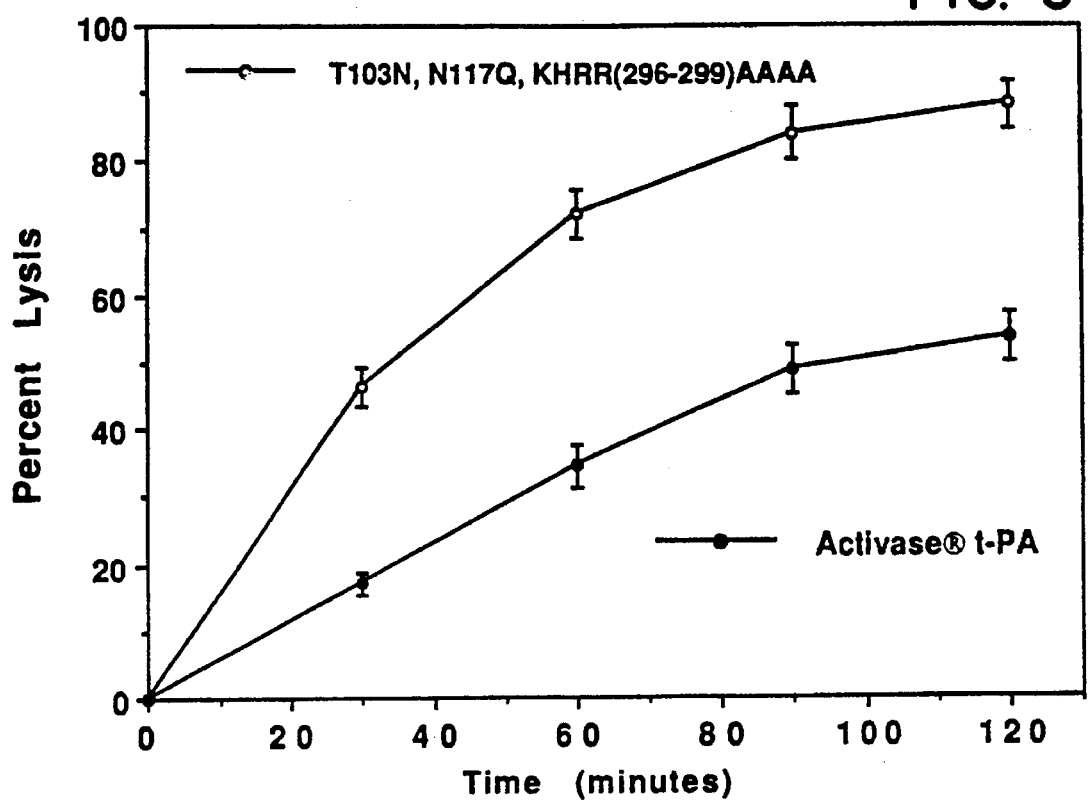
FIGS. 3, 4, 5 and 6 show the results of the in vivo clot lysis assay performed in a rabbit arterio-venous shunt thrombolysis model.

The terms "t-PA", "human t-PA", and "human tissue plasminogen activator" refer to human extrinsic (tissue-type) plasminogen activator having fibrinolytic activity that typically has a structure with five domains (finger, growth factor, Kringle-1, Kringle-2, and protease domains), but nonetheless may have fewer domains or may have some of its domains repeated if it still functions as a thrombolytic agent. At minimum, the t-PA consists of a protease domain that is capable of converting plasminogen to plasmin, and an N-terminal region believed to be at least partially responsible for fibrin binding. These terms thus include polypeptides containing these functional domains as part of the amino acid sequence of the polypeptide. Biologically active forms of t-PA may be produced by recombinant cell culture systems in forms comprising the two functional regions of the molecule and any other portions of t-PA otherwise native to the source of the t-PA. It will be understood that natural allelic variations exist and can occur among individuals, as demonstrated by one or more amino acid differences in the amino acid sequence of t-PA of each individual.

The terms "wild-type t-PA" "native t-PA" "wild-type human t-PA" and "native human t-PA" refer to native-sequence human t-PA, i.e., that encoded by the cDNA sequence reported in U.S. Pat. No. 4,766,075, issued 23 Aug. 1988. Amino acid site numbers or positions in the t-PA molecule are labeled in accordance with U.S. Pat. No. 4,766,075. The t-PA may be from any native source. In addition, the t-PA may be obtained from any recombinant expression system, including, for example, Chinese hamster ovary (CHO cells) or human embryonic kidney 293 cells.

The terms "fibrin binding" and "fibrin binding affinity" refer to the ability of the t-PA molecule to bind fibrin clots in standard fibrin binding assays, such as the method described by Rijken et al., *J. Biol. Chem.* 257, 2920–2925 (1982) or its modified version disclosed in Example 2.

The terms "(t-PA) biological activity", "biologically active", "activity" and "active" refer to the ability of the t-PA molecule to convert plasminogen to plasmin as measured in the S-2251 assay in the presence of a plasma clot or in the presence of fibrin, the S-2288 assay, the plasma clot lysis assay, or other appropriate assays. The assay (s) may be conducted in the presence or absence of potential modulators of activity such as fibrin, fibrinogen, plasma and/or plasma clots.

The expressions "fibrinolytic activity", "thrombolytic activity" and "clot lysis activity" are used interchangeably and refer to the ability of a t-PA molecule to lyse a clot, whether derived from purified fibrin or from plasma, using any in vitro clot lysis assay known in the art, such as the purified clot lysis assay by Carlson, R. H. et al., *Anal. Biochem.* 168, 428–435 (1988) and its modified form described by Bennett, W. F. et al., 1991, Supra.

The expressions "specific fibrinolytic activity", "specific thrombolytic activity" and "specific clot lysis activity" refer to clot lysis by unit steady state plasma level as determined by any in vitro clot lysis assay known in the art, such as those referred to above.

The expressions "in vivo fibrinolytic potency", in vivo thrombolytic potency" and "in vivo clot lysis potency" are used interchangeably and refer to clot lysis per unit dose of t-PA. "In vivo fibrinolytic potency" is determined in any accepted animal model of clot lysis assay, including the hamster pulmonary embolism model (Collen, D. et al., 1991, Supra), and the rabbit jugular vein thrombosis model [Collen, D. et al., *J. Clin. Invest.* 71, 368 (1983)]. A particularly preferred version of the latter model is described in the Example hereinbelow.

The expression "substantially retain fibrin binding (affinity)", (compared to wild-type human t-PA) and grammatical variants thereof as used herein mean that the fibrin binding affinity (apparent $K_d$ value) of the variant t-PA molecule is within about two fold of the fibrin binding affinity (kd value) for wild-type human t-PA as determined in the same assay. The expression "substantially improved fibrin binding" refers to a greater than about four fold increase in the fibrin binding affinity (apparent $k_d$ value) of a t-PA variant caused by the inclusion of an additional mutation or set of mutations. The term "improved in vivo fibrinolytic potency" compared to wild-type t-PA refers to comparable in vivo clot lysis achieved by the administration of a variant t-PA at about one-third or less the dose of wild-type t-PA.

The terms "clearance rate" and "clearance" refer to the rate at which the t-PA molecule is removed from the bloodstream. Clearance (rate) is measured with respect to native t-PA, such that decreased clearance (rate) indicates that the t-PA variant is cleared more slowly than native t-PA, and increased clearance (rate) indicates that the t-PA variant is cleared more rapidly than native t-PA.

The expression "fibrin specificity" refers to the activity of a mutant that exhibits a higher ratio of fibrin-dependent specific activity to fibrinogen-dependent specific activity in a S-2251 assay than wild-type human rt-PA, and preferably a ratio of at least 1.5.

The expression "plasma clot specificity" refers to the activity of a mutant that exhibits a higher ratio of plasma clot-dependent specific activity to plasma-dependent specific activity in a S-2251 assay than wild-type rt-PA, and preferably a ratio of at least 1.5.

The terms "zymogen," "zymogenic," and "zymogenic activity" are used herein as defined in WO 90/02798 published 22 Mar. 1990. According to this definition, the total absence of enzymatic activity is not a requirement.

The expression "devoid of functional carbohydrate structure at amino acid position 117 of wild-type human t-PA" means complete removal of the carbohydrate at amino acid residue 117, as where the glycosylation signal is destroyed by site-directed mutagenesis as described infra, or substantial removal, as by treatment with an endoglycosidase which may leave an intact N-acetylglucosamine residue linked to Asn 117, for example.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains.

They are broadly classified into two groups, charged and uncharged. Each of these groups is divided into subgroups to classify the amino acids more accurately:

I. Charged Amino Acids
  Acidic Residues: aspartic acid, glutamic acid
  Basic Residues: lysine, arginine, histidine
II. Uncharged Amino Acids
  Hydrophilic Residues: serine, threonine, asparagine, glutamine
  Aliphatic Residues: glycine, alanine, valine, leucine, isoleucine
  Non-polar Residues: cysteine, methionine, proline
  Aromatic Residues: phenylalanine, tyrosine, tryptophan The terms "alteration", "amino acid sequence alteration", "variant" and "amino acid sequence variant" refer to t-PA molecules with some differences in their amino acid sequences as compared to native t-PA. Ordinarily, the variants will possess at least 80% homology with those domains of native t-PA that are retained in their structure, and preferably, they will be at least about 90homologous with such domains. The glycosylation variants of t-PA falling within the scope of this invention optionally also contain substitutions, deletions, and/or insertions in addition to those resulting in the specified changes in the glycosylation pattern of t-PA.

Substitutional t-PA variants are those that have at least one amino acid residue in the native t-PA sequence removed and a different amino acid inserted in its place at the same position. The substitutions may be single, where only one amino acid in the molecule has been substituted, or they may be multiple, where two or more amino acids have been substituted in the same molecule.

Substantial changes in the activity of the t-PA molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the t-PA molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional t-PA variants are those with one or more amino acids inserted immediately adjacent to an amino acid at a particular position in the native t-PA molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native t-PA molecule removed. Ordinarily, deletional variants will have one or two amino acids deleted in a particular region of the t-PA molecule.

The notations used throughout this application to describe t-PA amino acid sequence variants are described below. the location of a particular amino acid in the polypeptide chain of t-PA is identified by a number. The number refers to the amino acid position in the amino acid sequence of the mature, wild-type human t-PA polypeptide as disclosed in U.S. Pat. No. 4,766,075, issued 23 Aug. 1988. In the present application, similarly positioned residues in t-PA variants are designated by these numbers even though the actual residue number is not so numbered due to deletions or insertions in the molecule. This will occur, for example, with site-directed deletional or insertional variants. The amino acids are identified using the one-letter code. Substituted amino acids are designated by identifying the wild-type amino acid on the left side of the number denoting the position in the polypeptide chain of that amino acid, and identifying the substituted amino acid on the right side of the number.

For example, replacement of the amino acid threonine (T) by asparagine (N) at amino acid position 103 of the wild-type human t-PA molecule yields a t-PA variant designated T103N t-PA. Similarly, the t-PA variant obtained by additional substitution of glutamine (Q) for asparagine (N) at amino acid position 117 of the wild-type human t-PA molecule is designated T103N, N117Q t-PA.

Deletional variants are identified by indicating the amino acid residue and position at either end of the deletion, inclusive, and placing the Greek letter delta, "Δ", to the left of the indicated amino acids. For example, a t-PA variant containing a deletion of amino acids 296–299 would be indicated as ΔK296-H297-R298-R299 t-PA, where K, H, and R indicate the amino acids lysine, histidine, and arginine, respectively. Deletion of a single amino acid, for example K296, would be indicated as ΔK296. Insertional t-PA variants are designated by the use of brackets "[]" around the inserted amino acids, and the location of the insertion is denoted by indicating the position of the amino acid on either side of the insertion. For example, an insertion of the amino acid alanine (A) between glutamic acid at position 94 and aspartic acid at position 95 would be indicated as E94 [A]D95. For ease of reading, comma "," is used to separate multiple mutations that occur in a single molecule, and a semi-colon ";" is used to separate individual t-PA variant molecules that have been constructed, where several t-PA variant molecules are listed together.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector"vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

Nucleic acid is "operably linked" when it is placed into a functional relationship with another nucleic acid sequence. For example, DNA for a presequence or secretory leader is operably linked to a DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

In the context of the present invention the expressions "cell", "cell line", and "cell culture" are used interchangeably, and all such designations include progeny.

The terms "transformed (host) cell", "transformant" and "transformed" refer to the introduction of DNA into a cell. The cell is termed a "host cell". The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA. The words transformants and transformed (host) cells include the primary subject cell and cultures derived therefrom, without regard to the number of transfers. It is also understood that all progeny may not be precisely identical in DNA content, due to deliberate or inadvertent mutations. Mutant progeny that have the same function or biological property as screened for in the originally transformed cell are included.

"Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

II. GENERAL METHODS

A. Selection Of Variants

Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation.

Glycosylation patterns for proteins produced by mammals are described in detail in *The Plasma Proteins: Structure, Function and Genetic Control*, Putnam, F. W., ed., 2nd edition, Vol. 4, Academic Press, New York, 1984, especially pp. 271–315. In this chapter, asparagine-linked oligosaccharides are discussed, including their subdivision into a least three groups referred to as complex, high mannose, and hybrid structures, as well as glycosidically linked oligosaccharides.

Glycosylation patterns for proteins produced by yeast are described in detail by Tanner and Lehle, *Biochim, Biophys, Acta*, 906(1), 915–944 (1987).

Typical N-linked glycosylation patterns of proteins produced from mammalian cells and yeast are compared in FIG. 1 of WO 89/11531 published 30 Nov. 1989.

Preliminary studies on the carbohydrate structures of native t-PA purified from Bowes melanoma cells (melanoma t-PA, mt-PA) demonstrated the presence of high-mannose oligosaccharides at position Asn 117, with complex-type oligosaccharides at positions Asn 184 and Asn 448 [Pohl et al., *Eur. J. Biochem.* 170, 69–75 (1987)]. Type I t-PA has all three N-linked positions substituted with carbohydrate, whereas Type II t-PA has no carbohydrate attached to position 184, accordingly, this position is only glycosylated in about 50% of the native t-PA molecules. One detailed report [Parekh et al., *Biochemistry* 28, 7644–7662 (1989)] confirmed these assignments, and additionally found that 30% of the oligosaccharides were sulfated.

The oligosaccharides for recombinant wild-type t-PA purified from transfected Chinese hamster ovary (CHO) cells (rt-PA or Activase® t-PA) have also been determined [Spellman et al., *J. Biol. Chem.* 264, 14100–14111 (1989)], and were found to have a similar pattern of glycosylation: high-mannose oligosaccharides at Asn 117, complex oligosaccharides at Asn 184 and Asn 448, with the Asn 184 site only glycosylated in 50% of the molecules.

The variants of this invention must contain at least one amino acid sequence that has the potential to provide glycosylation through an N- or O-linkage at any of amino acid positions 103, 104 and 105 of wild-type human t-PA.

If N-linked glycosylation is contemplated, the glycosylation site in the variant is a tripeptidyl sequence of the formula: asparagine-X-serine or asparagine-X-threonine, wherein asparagine in the acceptor and X is any of the twenty genetically encoded amino acids except proline, which is known to prevent glycosylation. See Struck, D. K. and Lennarz, W. J. in *The Biochemistry of Glycoproteins and Proteoglycans*, W. J. Lennarz ed., Plenum Press, 1980, p. 35; Marshall, R. D. *Biochem. Soc. Symp.* 40, 17 (1974); and Winzler, R. J. in *Hormonal Proteins and Peptides*, Li, C. I. ed., Academic Press, New York, 1973, pp. 1–15. The amino acid sequence variants herein are modified by either inserting the appropriate amino acid(s) at the proper site(s) to effect the glycosylation (as by adding the asparagine-X-serine/threonine tripeptide after position 103 to make the surface loop larger and more exposed) or substituting for the amino acid(s) at the appropriate site(s) the appropriate amino acids to effect glycosylation.

If O-linked glycosylation is to be employed, O-glycosidic linkage occurs in animal cells between N-acetylgalactosamine, galactose or xylose, and one of several hydroxyamino acids, most commonly serine or threonine, but also in some cases a 5-hydroxyproline or 5-hydroxylysine residue placed in the appropriate region of the molecule.

In one preferred embodiment, an N-linked glycosylation site is added at amino acid positions 103–105 of native human t-PA. For O-linked glycosylation, one or more amino acids in these regions are replaced or supplemented with serine, threonine, or 5-hydroxylysine residue.

Such t-PA variants are disclosed in WO 89/11531, supra, and in copending U.S. Pat. No. 5,270,198, supra.

The t-PA variants of the present invention are additionally characterized in lacking the functional carbohydrate structure at amino acid residue 117. According to a preferred embodiment, the functional carbohydrate structure is retained at all other amino acid positions glycosylated in the native t-PA molecule. Such selective removal of the functional carbohydrate structure at position 117 is preferably achieved by amino acid substitution for at least one residue in the Asn-Ser-Ser glycosylation signal at positions 117–119 of the wild-type human t-PA amino acid sequence. In a particularly preferred variant, asparagine (N) at amino acid position 117 is replaced by another amino acid, the preferred substituent being glutamine (Q) (see, e.g. EP 238,304, supra and copending U.S. Ser. No. 07/581,189 filed 10 Sep. 1990 which is a continuing application of Ser. No. 07/118,098 filed 6 Nov. 1987, now abandoned).

Preferred variants of the present invention have asparagine substituted for threonine at position 103, or for serine at position 105 in conjunction with substitution of serine for alanine at position 107 of native human t-PA, and have asparagine (N) at position 117 replaced by any other amino acid, the preferred substituent being glutamine (Q).

The plasminogen activators herein, in addition to the foregoing modifications in the glycosylation pattern of native t-PA, also optionally contain substitutions, deletions, or insertions of residues in other regions of the native t-PA sequence to improve certain properties of the molecule. Such modifications are well known in the art. A general review of plasminogen activators and second-generation derivatives thereof can be found in Harris, *Protein Engineering*, 1: 449–458 (1987) and Lijnen, H. R. and Collen, D., *Thromb. Haemost.* 66(1) 88–110 (1991). Other reviews of t-PA variants include Pannekoek et al., *Fibrinolysis*, 2: 123–132 (1988), Ross et al., in *Annual Reports in Medicinal Chemistry*, Vol. 23, Chapter 12 (1988), and Higgins and Bennett, 1990 supra.

For example, a means to further improve the clearance rate and/or half-life is the removal of part or all of the finger and/or growth factor domains from the t-PA variants of the present invention. Alternatively or in addition, the t-PA variants herein may exhibit resistance to proteolytic cleavage at or around amino acids 275 and 276 and/or having amino acid modifications in the putative lysine binding site of the kringle 2 domain of t-PA.

It was considered to be particularly desirable to provide t-PA variants that, in addition to their slower plasma clearance, are more fibrin specific than wild-type t-PA. Such t-PA variants will act more preferentially at the site of the fibrin clot than unmodified t-PA and are, therefore, expected to cause diminished side-effects associated with the activation of circulating plasminogen, e.g. less severe and less frequent bleeding complications.

The fibrin specificity of the t-PA variants of the present invention can be improved by any additional alteration known in the art.

In order to improve its fibrin specificity, a t-PA variant of the present invention can, for example, be further mutated at amino acid positions 296–302, preferably 296–299 of the serine protease domain. In a preferred variant, each of the amino acids lysine (K), histidine (H), arginine (R), arginine (R) at positions 296–299 of wild-type t-PA is replaced by alanine. In a further preferred variant, the arginines at positions 298 and 299 are both replaced by glutamic acid. In another preferred variant, the lysine (K), histidine (H), and proline (P) at amino acid positions 296, 297 and 301 of wild-type t-PA are additionally replaced by glutamine (Q), asparagine (N) and serine (S), respectively. In a further preferred embodiment, the fibrin specificity of the t-PA variants of the present invention is improved by replacing phenylalanine (F), arginine (R), isoleucine (I) and lysine (K) at amino acid positions 274, 275, 276 and 277 of the wild-type human t-PA amino acid sequence by amino acids leucine (L), histidine (H), serine (S) and threonine (T), respectively. The latter alteration results in a loss of plasmin cleavage site; therefore the variants are substantially in a single chain form.

In addition, the molecules of this invention may be substituted or may contain deletions at certain positions to confer additional desired properties including zymogenic character. These positions in human t-PA include, for example, substitution of alanine for lysine, histidine, and glutamic acid at positions 416–418, respectively, and substitution of alanine for glutamic acid, arginine, lysine, and glutamic acid at positions 426, 427, 429, and 430, respectively, as described, e.g., in WO 90/02798 published 22 Mar. 1990.

Examples of suitable multiple mutants are: T103N, N117Z t-PA; S105N, A107S, N117Z t-PA; T103N, N117Z, KHRR(296–299)AAAA t-PA; S105N, A107S, N117Z, KHRR(296–299)AAAA t-PA; T103N, N117Z, R298E, R299E t-PA; S105N, A107S, N117Z, R298E, R299E t-PA; T103N, N117Z, K296Q, H297N, P301S t-PA; S105N, A107S, N117Z, K296Q, H297N, P301S t-PA; T103N, N117Z, FRIK(274–277)LHST t-PA; S105, A107S, N117Z, FRIK(274–277)LHST t-PA, wherein Z denotes any of the 20 naturally occurring amino acids, except asparagine (N). Particularly preferred are the t-PA variants in which at position 117 asparagine (N) is substituted by glutamine (Q).

B. Construction Of Variants

The addition of extra glycosylation to the native t-PA molecule and the removal of functional carbohydrate structure at amino acid residue 117 can be accomplished by any methods known in the art.

Chemical and enzymatic coupling of glycosides to proteins can be accomplished using a variety of activated groups, for example, as described by Alpin and Wriston in *CRC Crit. Rev. Biochem.* pp. 259–306 (1981). The advantages of the chemical coupling techniques are that they are relatively simple and do not need the complicated enzymatic machinery required for natural O- and N-linked glycosylation. Depending on the coupling mode used, the sugar(s) may be attached to (a) arginine and histidine, (b) free carboxyl groups such as those of glutamic acid and aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987).

The carbohydrate structure at amino acid position 117 of native human t-PA can, for example, be substantially removed by the use of an endoglycosidase, such as Endoglycosydase H (Endo-H). Endo-H is only capable of (partial) removal of high mannose and hybrid oligosaccharides. Accordingly, under appropriate conditions, Endo-H is capable of (substantially) removing the high mannose carbohydrate structure at amino acid residue 117 (Asn) of native t-PA without functionally affecting the complex structures at amino acid residues 184 and 448. This treatment is accomplished via techniques known per se, for example, according to the method of Tarentino et al., *J. Biol. Chem.* 249, 811 (1974), Trimble et al., *Anal. Biochem.* 141, 515 (1984) and Little et al., *Biochem.* 23, 6191 (1984).

The t-PA variants of this invention are preferably constructed by mutating the DNA sequence that encodes wild-type t-PA, and expressing the mutated DNA sequence in an appropriate host cell.

The modification to change or insert the appropriate amino acid(s) in the native molecule to effect the desired sequence variations is accomplished by any means known in the art, such as e.g. site-directed mutagenesis or ligation of the appropriate sequence into the DNA encoding the relevant protein, as described below.

Whereas any technique known in the art can be used to perform site-directed mutagenesis, e.g. as disclosed in Sambrook et al. [*Molecular Cloning: A Laboratory Manual*, second edition, Cold Spring Harbor Laboratory Press, New York (1989)], oligonucleotide-directed mutagenesis is the preferred method for preparing the t-PA variants of this invention. This method, which is well known in the art [Adelman et al. *DNA,* 2:183 (1983), Sambrook et al., Supra], is particularly suitable for making substitution variants, it may also be used to conveniently prepare deletion and insertion variants.

The oligonucleotides are readily synthesized using techniques well known in the art such as that described by Crea et al. (*Proc. Nat'l. Acad. Sci. USA,* 75:5765 [1978]).

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotides is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Another method for making mutations in the DNA sequence encoding wild-type t-PA or a variant molecule known in the art, for example to introduce a new glycosylation site in accordance with the present invention involves cleaving the DNA sequence encoding the starting t-PA molecule at the appropriate position by digestion with restriction enzymes, recovering the properly cleaved DNA, synthesizing an oligonucleotide encoding the desired amino acid sequence for glycosylation and flanking regions such as polylinkers with blunt ends (or, instead of polylinkers, digesting the synthetic oligonucleotide with the restriction enzymes also used to cleave the t-PA encoding DNA, thereby creating cohesive termini), and ligating the synthetic DNA into the remainder of the t-PA encoding structural gene.

PCR mutagenesis is also suitable for making the t-PA variants of the present invention, for example, as described in U.S. Pat. No. 4,683,195 issued 28 Jul. 1987 and in *Current Protocols in Molecular Biology,* Ausubel et al., eds. Greene Publishing Associates and Wiley-Interscience, Volume 2, Chapter 15, 1991.

The cDNA encoding the t-PA variants of the present invention is inserted into a replicable vector for further cloning or expression.

Suitable vectors are prepared using standard recombinant DNA procedures. Isolated plasmids and DNA fragments are cleaved, tailored, and ligated together in a specific order to generate the desired vectors.

After ligation, the vector with the foreign gene now inserted is transformed into a suitable host cell. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.,* 9:309 (1981) or by the method of Maxam et al., *Methods of Enzymology,* 65:499 (1980).

Prokaryotes are the preferred host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC number 31,446), *E. coli* strain W3110 (ATCC number 27,325) *E. coli* X1776 (ATCC number 31,537), and *E. coli* B; however many other strains of *E. coli*, such as HB101, JM101, NM522, NM538, NM539, and many other species and genera of prokaryotes may be used as well. These are, of course, intended to be illustrative rather than limiting.

Plasmid vectors containing replicon and control sequences that are derived from species compatible with the host cell are used with these hosts. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUC118, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature,* 375:615 [1978]; Itakura et al., *Science,* 198:1056 [1977]; Goeddel et al., *Nature,* 281:544 [1979]) and a tryptophan (trp) promoter system (Goeddel et al., *Nucl. Acids Res.,* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell,* 20:269 [1980]).

For expression of the t-PA variants of the present invention eukaryotic hosts, such as eukaryotic microbes (yeast) and multicellular organisms (mammalian cell cultures) are used.

*Saccharomyes cerevisiae,* or common baker's yeast, is the most commonly used among lower eukaryotic host microorganisms. However, a number of other genera, species, and strains are commonly available and useful herein, such as *Schizosaccharomyces pombe* [Beach and Nurse, *Nature,* 290: 140 (1981); EP 139, 383 published May 2, 1985]; Kluyveromyces hosts (U.S. Pat. No. 4,943,529; Fleer et al., supra) such as, e.g., *K. lactis* [MW98-8C, CBS683, CBS4574; Louvencourt et al., *J. Bacteriol.,* 737 (1983)], *K. fragilis* (ATCC 12,424), *K. bulgaricus* (ATCC 16,045), *K. wickeramii* (ATCC 24,178); *K. waltii* (ATCC 56,500), *K. drosophilarum* (ATCC 36,906; Van den Berg et al., supra), *K. thermotolerans*, and *K. marxianus; varrowia* [EP 402, 226]; *Pichia pastoris* [EP 183,070; Sreekrishna et al., *J. Basic Microbiol.,* 28: 265–278 (1988)]; *Candida; Trichoderma reesia* [EP 244,234]; *Neurospora crassa* [Case et al., *Proc. Natl. Acad. Sci. USA,* 76: 5259–5263 (1979)]; Schwanniomyces such as *Schwanniomyces occidentalis* [EP 394,538 published 31 Oct. 1990]; and filamentous fungi such as, e.g., Neurospora, Penicillium, Tolypocladium [WO 91/00357 published 10 Jan. 1991], and Aspergillus hosts such as *A. nidulans* [Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

Suitable promoting sequences in yeast vectors include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; Holland et al., *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms may be used as hosts to practice this invention. While both invertebrate and vertebrate cell cultures are acceptable, vertebrate cell cultures, particularly mammalian cultures, are preferable. Examples of suitable cell lines include monkey kidney CVI line transformed by SV40 (COS-7, ATCC CRL 1651); human embryonic kidney line 293S (Graham et al., *J. Gen. Virol.*, 36:59 [1977]); baby hamster kidney cells (BHK, ATCC CCL 10); Chinese hamster ovary (CHO) cells (Urlab and Chasin, *Proc. Natl. Acad. Sci USA*, 77:4216 [1980]); mouse sertoli cells (TM4, Mather, *Biol. Reprod.*, 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.*, 85:1 [1980]); and TRI cells (Mather et al., *Annals N. Y. Acad. Sci.*, 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature*, 273:113 [1978]). Smaller or larger SV40 DNA fragments may also used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of human t-PA are produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells.

Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin (*Proc. Natl. Acad. Sci. (USA)* 77:4216 [1980]) are transformed with wild-type DHFR coding sequences. After transformation, these DHFR-deficient cell lines express functional DHFR and are capable of growing in a culture medium lacking the nutrients hypoxanthine, glucine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC number CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

The mammalian host cells used to produce the variants of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace (*Meth. Enz.*, 58: 44 [1979]), Barnes and Sato (*Anal. Biochem.*, 102: 255 [1980]), U.S. Pat. Nos. 4,767,704; 4,657,866; 4,927,762; or 4,560,655; WO 90/03430; WO 87/00195; U.S. Pat. No. Re. 30,985; or copending U.S. Ser. No. 07/592,107 or 07/592,141, both filed in Oct. 3, 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium and phosphate), buffers (such as HEPES), nucleosides (such as adenosine and thymidine), antibiotics (such as Gentamycin), trace elements (defined as inorganic compounds usually present at final concentrations in the micromolar range), and glucose or an equivalent energy source. Any other necessary supplements may also be included at appropriate concentrations that would be known to those skilled in the art.

Many eukaryotic proteins normally secreted from the cell contain an endogenous signal sequence as part of the amino acid sequence. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, alanine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the 'pre-protein' or the immature form of the protein.

However, not all secreted proteins contain an amino terminal signal sequence that is cleaved. Some proteins, such as ovalbumin, contain a signal sequence that is located on an internal region of the protein. This sequence is not normally cleaved during translocation.

Proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA encoding the signal sequence portion of the gene is excised using appropriate restriction endonucleases and then ligated to the DNA encoding the protein to be secreted, i.e. t-PA.

Selection of a functional signal sequence requires that the signal sequence is recognized by the host cell signal peptidase such that cleavage of that signal sequence and secretion of the protein will occur. The DNA and amino acid sequence encoding the signal sequence portion of several eukaryotic genes including, for example, human growth hormone, proinsulin, and proalbumin are known (see Stryer, *Biochemistry*, W. H. Freeman and Company, New York [1988], p. 769) and can be used as signal sequences in appropriate eukaryotic host cells. Yeast signal sequences, as for example acid phosphatase (Arima et al., *Nuc. Acids Res.*, 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 1988]), MalE, PhoA, or beta-lactamase, as well as other genes, may be used to target proteins from prokaryotic cells into the culture medium.

An alternative technique to provide a protein of interest with a signal sequence such that it may be secreted is to chemically synthesize the DNA encoding the signal sequence. In this method, both strands of an oligonucleotide encoding the selected signal sequence are chemically synthesized and then annealed to each other to form a duplex. The double-stranded oligonucleotide is then ligated to the 5' end of the DNA encoding the protein.

The construct containing the DNA encoding the protein with the signal sequence ligated to it can then be ligated into a suitable expression vector. This expression vector is transformed into an appropriate host cell and the protein of interest is expressed and secreted.

Cultures of mammalian host cells and other host cells that do not have rigid cell membrane barriers are usually transformed using the calcium phosphate method as originally described by Graham and Van der Kb (*Virology*, 52:546 [1978]) and modified as described in sections 16.32–16.37 of Sambrook et al. supra. However, other methods for introducing DNA into cells such as Polybrene (Kawai and Nishizawa, *Mol. Cell. Biol.*, 4:1172 [1984]), protoplast fusion (Schaffner, *Proc. Natl. Acad. Sci. USA*, 77:2163 [1980]), electroporation (Neumann et al., *EMBO J.*, 1:841 [1982]), and direct microinjection into nuclei (Capecchi, *Cell*, 22:479 [1980]) may also be used.

Yeast host cells are generally transformed using the polyethylene glycol method, as described by Hinnen (*Proc. Natl. Acad. Sci.* U.S.A., 75:1929 [1978]).

Prokaryotic host cells or other host cells with rigid cell walls are preferably transformed using the calcium chloride method as described in section 1.82 of Sambrook et al., supra. Alternatively, electroporation may be used for transformation of these cells.

The t-PA variant preferably is recovered from the culture medium as a secreted protein, although it also may be recovered from host cell lysates when directly expressed without a secretory signal. When the variant is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

The variant is then purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis. A protease inhibitor that does not interfere with the t-PA activity such as phenylmethylsulfonyl fluoride (PMSF) also may be useful to inhibit proteolytic degradation during purification, and antibiotics may be included to prevent the growth of adventitious contaminants. One skilled in the art will appreciate that purification methods suitable for native t-PA may require modification to account for changes in the character of t-PA or its variants upon expression in recombinant cell culture.

In a preferred embodiment, the t-PA variant is secreted, the harvested cell culture fluid is diafiltered, and the t-PA variant is purified using lysine affinity chromatography. Alternatively, the supernatant of the cell culture may be passed over a PBS-preconditioned column of glass beads coupled to anti t-PA goat polyclonal A6 antibody, followed by equilibration of the column with a buffer, and elution of the t-PA variant.

The compounds of the present invention can be formulated according to known methods to prepare pharmaceutically useful compositions, whereby the t-PA product is combined in admixture with a pharmaceutically acceptable carrier. Suitable carriers and their formulations are described in *Remington's Pharmaceutical Sciences*, 16th ed., 1980, Mack Publishing Co., edited by Oslo et al., specifically incorporated by reference. These compositions will typically contain an effective amount of the t-PA variant, for example, from on the order of about 0.5 to about 5 mg/ml, together with a suitable amount of carrier to prepare pharmaceutically acceptable compositions suitable for effective administration to the patient. The t-PA variant may be administered parenterally to patients suffering from cardiovascular diseases or conditions, or by other methods that ensure its delivery to the bloodstream in an effective form.

Compositions particularly well suited for the clinical administration of the t-PA variants used to practice this invention include sterile aqueous solutions or sterile hydratable powders such as lyophilized protein. Typically, an appropriate amount of a pharmaceutically acceptable salt is also used in the formulation to render the formulation isotonic. A buffer such as arginine base in combination with phosphoric acid is also typically included at an appropriate concentration to maintain a suitable pH, generally from 5.5 to 7.5. In addition or alternatively, a compound such as glycerol may be included in the formulation to help maintain the shelf-life.

Dosages and desired drug concentrations of pharmaceutical compositions of this invention may vary depending on the particular variant and the particular use envisioned. The determination of the appropriate dosage is well within the skill of a physician, especially in view of the extensive experience with the administration of wild-type recombinant human t-PA. Due to their prolonged plasma half-lives, the t-PA variants of the present invention are particularly suitable for bolus administration. According to a preferred mode of administration, the t-PA variants of the present invention are administered in an initial intravenous bolus dose substantially saturating t-PA clearance mechanism, as disclosed in copending Application Ser. No. 07/841,698 filed 26 Feb. 1992, optionally followed by further bolus and/or continuous intravenous administrations. For variants with biological activity comparable to that of wild type t-PA, the total dose preferably is about 100 mg. More active variants achieve the same effect at lower doses. Variants with improved fibrin specificity may be administered at higher doses without significantly increasing the risk of bleeding complications.

As a general rule, dosage and dose rate may be parallel to or higher than that currently in use in clinical investigations of other cardiovascular, thrombolytic agents, e.g., about 1–2 mg/kg body weight as an intravenous or intra-arterial dose over 1.5 to 12 hours in human patients suffering from myocardial infarction, pulmonary embolism, etc.

For example, in the treatment of deep vein thrombosis or peripheral vascular disease, "bolus" doses, on the order of about 0.05 to about 0.2 mg/kg, will typically be preferred with subsequent administrations of on the order of about 0.1 to about 0.2 mg/kg administered to maintain a fairly constant blood level, preferably of on the order of about 3 μg/ml.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variants of this invention are also useful for preventing fibrin deposition or adhesion formation or reformation. One embodiment of this use is described in EPO 297,860 published 4 Jan. 1989. Generally, this type of treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Usually, this amount is from 0.02 mg/g of gel to 25 mg/g of gel, with preferred amounts from 0.20 mg/g gel to about 2.5 mg/g gel, most preferably from 0.25 mg/g gel to about 1.0 mg/g gel. Each t-PA variant used to prevent adhesion formation and/or fibrin deposition is typically formulated in a semi-solid, mucilagenous, pharmaceutically inert carrier for positioning the enzyme at the site of potential adhesion formation. The carrier includes long-chain hydrocarbons or vegetable oils and waxes composed of mixtures of modified saturated and unsaturated fatty acid glycerides or mixtures of modified saturated and unsaturated fatty acid glycerides. Examples include semi-solid vehicles such as petroleum jelly or semi-synthetic glycerides, polyhydroxy solvents such as glycerol, long-chain hydrocarbons, bioerodable polymers, or liposomes.

The following examples merely illustrate the best mode now contemplated for practicing the invention, but should not be construed to limit the invention.

EXAMPLE 1

Recombinant Production of the t-PA Variants

I. Vector Construction and Mutagenesis

The new t-PA variants of the present invention were constructed in t-PA expression vector pRK7-t-PA (see e.g. WO 90/02798, published 22 Mar. 1990, and WO 92/02612 published 20 Feb. 1992). This vector containing mutant or wild-type t-PA was used for transfection and expression in human embryonic kidney cells (293c).

Site-directed mutagenesis of t-PA cDNA was performed by the method of Taylor et al., *Nucl. Acids. Res.*, 13: 8765 (1985) using a kit purchased from the Amersham Corporation (catalog number RPN 1253). For generation of the desired mutants, oligonucleotides of sequences coding for the desired amino acid substitutions were synthesized and used as primers. These oligonucleotides were annealed to single-stranded pRK7-t-PA that had been prepared by standard procedures [Viera et al., *Meth. Enz.*, 143:3 (1987].

Some of the t-PA variants were generated using the Kunkel mutagenesis [Kunkel, T. A., *Proc. Natl. Acad. Sci. USA* 82, 488–492 (1985) and Kunkel, T. A. et al., *Meth. Enzymol*, 154, 367–382 (1987)].

A mixture of three deoxyribonucleotides, deoxyriboadenosine (dATP), deoxyriboguanosine (dGTP), and deoxyribothymidine (dTTP), was combined with a modified thiodeoxyribocytosine called dCTP (aS) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the mutated bases was generated. In addition, this new strand of DNA contained dCTP (aS) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

The oligonucleotides used as primers to generate pRK7-t-PA molecules are shown in the following Table 1:

TABLE 1

| Mutation (single locus) a | Oligonucleotide Sequence (reading 5' to 3') |
| --- | --- |
| T103N | TGTGCTCCAATTGCCCCTGTAGCT (SEQ. ID. NO: 1) |
| S105N,A107S | GCCACTCTCGGATGTATTCCACGTGCCCCT (SEQ. ID. NO: 2) |
| N117Q | CGCGCTGCTTTGCCAGTTGGTGCA (SEQ. ID. NO: 3) |
| KHRR(296–299)AAAA | CCGCTCTCCGGGCGACGCCGCGGCCGCGGCAAAGAT (SEQ. ID. NO: 4) | a Single locus mutants is a term describing t-PA variants that were made by mutagenesis with a single oligonucleotide using wildtype t-PA as a template.

Although the variants S105N,A107S t-PA and KHRR(296–299)AAAA t-PA are multiple mutants, as they contain more than one amino acid substitution, they were each generated using only one oligonucleotide. This was possible since the substituted amino acids are located very close to each other in the polypeptide chain.

A slight variation of the above described procedure was employed to prepare additional multiple mutants. For the mutants described below, the template DNA was not wild-type t-PA (pRK7-t-PA). Instead, the templates used were those that contained at least a single mutation, i.e. the DNA produced in construction of the mutants in Table 1 above. The DNA used as the template, and the oligonucleotide used to generate the additional mutations for each "double loci" mutant made is listed in Table 2 below. The DNA sequence of each oligonucleotide is set forth in Table 1 above. The asterisks indicate variants that are illustrative of this invention.

TABLE 2

| Mutants (double loci) b | Template | Oligonucleotide |
| --- | --- | --- |
| T103N, N117Q* | T103N | N117Q |
| S105N, A107S, N117Q* | S105N, A107S | N117Q |
| T103N, KHRR(296–299)AAAA | KHRR(296–299)AAAA | T103N |
| S105N, A107S, KHRR(296–299)AAAA | KHRR(296–299)AAAA | S105N, A107S |
| N117Q, KHRR(296–299)AAAA | KHRR(296–299)AAAA | N117Q | b Double loci mutants were produced with DNA coding for a single locus mutant of t-PA as a template for mutagenesis.

The following multiple ("triple loci") mutants were generated essentially following the foregoing procedure, using the multiple mutants indicated in the template column as templates. The sequence of each oligonucleotide is set forth in Table 1 above. The asterisks indicate variants that are illustrative of this invention.

TABLE 3

| Mutants (triple loci) c | Template | Oligonucleotide |
| --- | --- | --- |
| T103N, N117Q, KHRR(296–299)AAAA* | N117Q,KHRR(296–299)AAAA | T103N |
| S105N, A107S, N117Q, KHRR(296–299)AAAA* | S105N,A107S,N117Q,KHRR | N117Q | c Triple loci mutants were produced with DNA coding for a double loci mutant of t-PA as a template for mutagenesis.

II. Bacterial Transformation and DNA Preparation

The mutant t-PA constructs generated using the protocol above were transformed into E. coli host strain MM294tonA using the standard CaCl$_2$ procedure (Sections 1.76–1.84 Sambrook et al., Supra) for preparation and transformation of competent cells. The E. coli strain MM294tonA (which is resistant to T1 phage) was prepared by the insertion and subsequent imprecise excision of a Tn10 transposon into the tonA gene. This gene was then inserted, using transposon insertion mutagenesis [Kleckner et al., J. Mol. Biol., 116: 125–159 (1977)], into E. coli host MM294 (ATCC 31,446).

DNA was extracted from individual colonies of bacterial transformants using the standard miniprep procedure of Maniatis et al., Supra. The plasmids were further purified by passage over a Sephacryl CL6B spin column, and then analyzed by sequencing and by restriction endonuclease digestion and agarose gel electrophoresis.

Alternatively, the sequence was determined at the single-strand level, and the double-stranded plasmids were purified from the bacterial transformants by a Qiagen plasmid kit, following the manufacturer's instructions.

III. Transformation of Human Embryonic Kidney 293 Cells

Human embryonic kidney 293 cells were grown to 70% confluence in 6-well plates. 2.5 μg of plasmid encoding the t-PA mutant was dissolved in 150 μl of 1 mM Tris-HCl, 0.1 mM EDTA, 0.227M CaCl$_2$. Added to this (dropwise while vortexing) was 150 μl of 50 mM HEPES buffer (pH 7.35), 280 mM NaCl, 1.5 mM NaPO$_4$, and the precipitate was allowed to form for ten min. at 25° C. The suspended precipitate was then added to the cells in the individual wells in the 6-well plate and allowed to settle overnight in the incubator. The medium was then aspirated off and 1 ml of 20% glycerol in PBS (phosphate buffered saline) was added. Then 3 ml of fresh serum-free medium was added and the cells were incubated for five days. The medium was then collected and assayed.

The transfection for large-scale production and purification of the t-PA variants of the present invention in 293 cells can, for example, be performed as described in WO 90/02798, Supra.

IV. Expression and Purification in Chinese Hamster Ovary (CHO) Cells

The broadly applicable parental vector pSVI6B5 (transformed E. coli strain ATCC No. 68,151) was used for transfection and expression of the t-PA variants of the present invention in Chinese Hamster Ovary (CHO) cells. The construction of pSVI6B5 is disclosed in U.S. application Ser. No. 07/441,574, filed 22 Nov. 1989, now abandoned, and in U.S. Pat. No. 5,087,572 issued 11 Feb. 1992.

CHO-dhfr⁻ cells (such as those described by Urlaub and Chasin, Supra), which has been grown on non-selective medium, were cotransfected with a pSVI6B5 based expression vector in which the cDNA sequence encoding the desired t-PA variant had been inserted at the polylinker site, and with a dhfr selection vector PFD11 [Simonsen and Levinson, *Proc. Natl. Acad. Sci. USA* 80, 2495–1499 (1983)], using the general procedure of Graham and van der Eb, Supra. Following transfection, the cells were exposed to selective medium: either a) lacking glycine, hypoxanthine, and thymidine, or b) lacking these components and supplemented with methotrexate at concentrations ranging from 10 to 300 nM. About 50 colonies were isolated for each transfection, preferentially from those plates which exerted the highest stringency of selection (with methotrexate). The clones were expanded into 6 well plates for analysis of expression of recombinant t-PA variant. Confluent wells were exposed to serum free production medium (modified from DMEM/F12 1:1 containing insulin and transferrin) for 5–6 days, and the t-PA in the cell culture fluid was quantitated using a polyclonal based ELISA assay. The best producing clone for each transfection was expanded for scale-up and production. The cells were adapted to growth in suspension and the t-PA variants were produced in spinner cultures using serum-free medium. The harvested cell culture fluid was diafiltered, and the t-PA variant was purified using lysine affinity chromatography.

EXAMPLE 2

Characterization of the t-PA Variants 1. t-PA Quantitation

Protein concentrations were routinely determined by an ELISA standardized to native-sequence t-PA (See EPO Pat. Publ. 93,619). Protein purity and homogeneity were analyzed by polyacrylamide gel electrophoresis in the presence of sodium dodecyl sulfate (PAGE-SDS) with the buffer system of Laemmli, *Nature*, 227: 680 (1970). Typically, 10 to 20% gradient gels were used and proteins were visualized with either Coomassie blue or the silver-staining technique of Morrissey, *Anal. Biochem.*, 117: 307 (1981). The t-PA variant prepared as described above was found to be pure and homogeneous by this method.

2. Labeling of t-PA Variants for Clearance and Binding Studies

The active site labeling agent was prepared by Chloramine-T-catalyzed radioiodination of tyrosyl-prolyl-arginyl chloromethylketone (YPRck), using a modification of the method described by Hunter and Greenwood [*Nature* 194, 495–496 (1962)]. In a typical reaction, 50 µl of 1M Tris-HCl a pH 7.5 was added to 40 µl of Na$^{125}$I (4 mCi; 1.8 nmol) in a capped reaction vessel. To this vessel, 8.3 µl of YPRck (1.8 nmol in 12 nM HCl) was added. Iodination was initiated by addition of 12.5 µl Chloramine-T (1 mg/ml in 0.1M NaP$^i$, pH 7.5). Iodination was quenched after 60 s at 24° C. with 25 µl of sodium metabisulfite (a mg/ml in 0.1M NaP$_i$, pH 7.5). The reaction was then diluted by addition of 2 ml of PBS, and 20 µl aliquots of the diluted labeled reagent were added to 1 ml aliquots of the culture supernatants of transiently transfected 293 cells. This mixture was incubated for one hour, and the free $^{125}$I was separated from the protein-bound $^{125}$I by gel filtration on a PD-10 column (Pharmacia). Protein-bound $^{125}$I was determined by precipitation with 10% trichloroacetic acid. These labeling conditions were optimized for a 1:1:1 molar ratio of iodine:YPRck:t-PA. The specific radioactivity of the $^{125}$I-labeled t-PA variants was about 1 µCi $^{125}$I/µg t-PA.

3. Evaluation of Clearance Rate

Plasma Clearance in Mice

The clearance rate of the t-PA variants was assessed by radiolabeling human embryonic kidney 293 cell derived protein, injecting it into mice, and measuring the radioactivity in the blood of the mice over time. Each experiment involved four mice. The mice were divided into two groups, and both mice in a group were bled at predetermined time points. The data from the two groups were combined and plotted on a graph of time versus cpm in the blood. The area under the plasma disposition curve (AUC) for each mouse was computed using successive trapezoids from 1 to 40 minutes.

In the following table,

N indicates the number of experiments used to determine the clearance rate.

Mean±Std. Dev. represents the clearance rate expressed in ml/min/kg (of body weight), calculated by the area under the plasma disposition curve as described above.

% C.V. is the coefficient of variation value as a percentage.

Norm. is normalized factor which represents the ratio of the clearance for a t-A variant compared to the clearance of wild-type (293 cell derived) t-PA.

The asterisks indicate variants that are illustrative of this invention.

TABLE 4

| Plasma Clearance in Mice | | | | |
|---|---|---|---|---|
| t-PA Variants | N | Mean ± Std. Dev. | % C.V. | Norm. |
| Wild-type t-PA | 12 | 34.3 ± 4.9 | 14.3 | 1.00 |
| T103N | 5 | 14.4 ± 1.5 | 10.1 | 0.42 |
| S105N, A107S | 3 | 20.0 ± 2.6 | 12.9 | 0.58 |
| N117Q | 4 | 20.2 ± 3.7 | 18.6 | 0.59 |
| KHRR | 3 | 35.0 ± 5.2 | 15.1 | 1.02 |
| T103N, N117Q* | 3 | 10.5 ± 2.3 | 21.8 | 0.31 |
| S105N, A107S, N117Q* | 3 | 12.1 ± 2.2 | 18.3 | 0.35 |
| T103N, KHRR | 4 | 14.4 ± 1.6 | 10.8 | 0.42 |
| S105N, A107S, KHRR | 2 | 19.2 ± 0.8 | 4.2 | 0.56 |
| N117Q, KHRR | 5 | 20.3 ± 3.9 | 19.4 | 0.59 |
| T103N, N117Q, KHRR* | 2 | 9.7 ± 0.7 | 7.3 | 0.28 |
| S105N, A107S, N117Q, KHRR* | 1 | 10.0 n.a. | n.a. | 0.30 |

KHRR = KHRR(296–299)AAAA t-PA

Plasma Clearance in Rabbits

Pharmacokinetic analysis of t-PA and t-PA variants in rabbits was done using the experimental protocol of the arterial-venous shunt (AVS) model of thrombolysis described on Section 5 hereinafter. A 20G Teflon catheter with flowswitch (Viggo) was placed in the medial ear artery of anaesthetized male New Zealand White rabbits weighing 2.5–3.5 kg each. A 22G catheter fitted with an injection cap was placed in the marginal vein of the opposite ear. The catheters were flushed and locked with heparinized saline.

Activase® t-PA or the t-PA variants were given as a bolus or infused via the venous catheter. The intravenous infusion was initiated with a 15% loading bolus followed by an infusion of the remaining 85% of the dose over 120 minutes. Various doses of Activate® t-PA or the t-PA variants were tested in the AVS protocol: 60 µg/kg, 180 µg/kg and 540 µg/kg. The variant T103N, KHRR(296–299)AAAA was tested at four doses: 20 µg/kg, 60 µg/kg, 180 µg/kg and 540 µg/kg. Blood samples were taken at 30 min., 60 min., and 90 min. during the infusion protocol. Samples were taken at 2, 10, 20, 30, 45, 60, 90, and 120 minutes after the administration by bolus injection. Anti-coagulated plasma was prepared from the blood samples and the t-PA or t-PA variant concentration in plasma was determined by a polyclonal ELISA. The values of clearance rate for five animals were evaluated at each of the multiple doses.

The plasma clearance of the t-PA variants of the present invention in comparison with Activase® t-PA and known t-PA variants is shown in the following Table 5. The asterisk indicates a variant that is illustrative of this invention.

TABLE 5

| | Plasma Clearance in Rabbits (ml/min/kg) | |
|---|---|---|
| t-PA Sample | Infusion[a] | Bolus[b] |
| Activase ® t-PA | 20.7 ± 3.9 | 23.9 ± 6.4 |
| KHRR(296–299)AAAA | 20.0 ± 3.0 | n.d. |
| T103N | n.d. | 2.7 ± 0.4 |
| T103N, KHRR(296–299)AAAA | n.d. | 3.3 ± 0.2 |
| N117Q, KHRR(296–299)AAAA | n.d. | 22.7 ± 1.2 |
| T103N, N117Q, KHRR(296–299)AAAA* | n.d. | 2.1 ± 0.4 |

[a]For those t-PA variants which lacked mutations associated with reduced clearance [i.e. wild-type and KHRR(296–299)AAAA], the plasma clearance was evaluated after a constant intravenous infusion of the protein. The steady state plasma concentration of the t-PA variant was determined at the end of the infusion with a polyclonal ELISA. The clearance was calculated by the following relationship: Clearance = infusion rate/steady state plasma concentration. Average clearance rates (± std. dev.) were determined with replicate analyses (n = 33 and n = 19) for Activase ® and KHRR[296–299] AAAA, respectively.
[b]t-PA variants with slow clearance characteristics (and Activase ® t-PA) were evaluated in rabbits after a bolus administration of the protein by intravenous injection. The plasma concentration of t-PA at various times after injection was determined using a polyclonal ELISA. The clearance rate was calculated with the relationship: Clearance rate = Dose/area under the plasma disposition curve. Average clearance rates (± std. dev.) were determined with replicate analyses (n = 5, 15, 16, 15, and n = 10) for Activate ®; T103N; T103N, KHRR(296–299)AAAA; N117Q, KHRR(296–299)AAAA; and T103N, N117Q, KHRR(296–299)AAAA, respectively.

4. Fibrin Binding

Purified t-PA mutants from CHO cells were radiolabeled with $I^{125}$-YPRck and converted to the two-chain form with soluble plasmin using the following procedure. Aliquots (1.5 ml) containing 0.15 µCi of $I^{125}$-YPRck labeled t-PA (or variants), in phosphate buffered saline with 0.5% bovine serum albumin and 0.01% Tween 80, were incubated with human plasmin (0.09 casein units in 15 µl of phosphate buffered saline) for two hours at 25° C. with gentle shaking. Residual plasmin was inhibited with aprotinin by the addition of 0.9 TI units in 15 µl of phosphate buffered saline.

Fibrin binding was evaluated using a modification of the method described by Rijken et al., *J. Biol. Chem.*,257: 2920–2925 (1982). Dilutions of lysine-Sepharose treated human fibrinogen ranging from 0.12 µg/ml to 8 mg/ml were prepared in phosphate buffered saline. Aliquots of fibrinogen (50 µl) and $I^{125}$-YPRck labeled t-PA or variants (100 µl) were combined in 1.2 ml polypropylene tubes and mixed briefly. Fibrin clots were formed by the addition of human thrombin (50 µl of 1 unit/ml.) and were visible within 60 seconds. After 60 minutes at room temperature, the clots were centrifuged at 13000 rpm for 5 minutes at 4° C. Aliquots of supernatants (50 µl) were transferred to individual tubes for counting. To account for the total radioactivity, the original polypropylene tubes (containing the clots and the remaining liquid) were also counted. The amount of bound t-PA was the difference between the total radioactivity (sum of the 50 µl aliquot and the tubes containing the clot) and the unbound radioactivity which was calculated as 4 fold the amount in 50 µl of supernatant.

Results of the fibrin binding assay performed with CHO-derived purified, plasmin-treated material are shown in FIGS. 1 and 2. The numerical fibrin binding data for two-chain t-PA (and t-PA variants) are set forth in the following Table 6. The asterisks indicate variants that are illustrative of this invention.

TABLE 6

| | Fibrin Binding Assay[a] | |
|---|---|---|
| t-PA Sample | [Fibrin]50 (µg/ml)[b] | app $K_d$ (µM)[c] |
| Activase ® t-PA | 72 | 0.21 |
| KHRR(296–299)AAAA | 87 | 0.26 |
| T103N | 830 | 2.5 |
| T103N, N117Q* | 63 | 0.19 |
| T103N, KHRR(296–299)AAAA | 620 | 1.8 |
| T103N, N117Q, KHRR(296–299)AAAA* | 120 | 0.35 |
| S105N, A107S | 210 | 0.63 |
| S105N, A107S, N117Q* | 97 | 0.29 |
| S105N, A107S, N117Q, KHRR(296–299)AAAA* | 85 | 0.25 |

[a]The YPRck-labeled samples of t-PA were treated with plasmin. This binding assay measures the fibrin affinity of t-PA in the two-chain form.
[b][Fibrin]50 represents the concentration of fibrin required to observe 50% of the sample protein bound to fibrin.
[c]app $K_d$ represents the apparent affinity constant of t-PA binding to a fibrin clot as determined by the micromolar concentration of fibrin required to bind 50% of the t-PA. The molecular weight of fibrin monomer used in this calculation was 340 kilodaltons.

As apparent from the above data and FIG. 1, the T103N mutation adding an (extra) glycosylation site at position 103 of the wild-type human t-PA molecule results in a significant loss of fibrin binding. Even though T103N t-PA has been shown to exhibit an about 3 to 5-times reduced clearance as compared to wild-type human t-PA, its therapeutic value is not significantly improved due to the loss in fibrin binding.

As demonstrated by the foregoing data and shown in FIG. 2, the fibrin binding of T103N t-PA is substantially improved by adding a second mutation resulting in the removal of glycosylation of position 117 of the wild-type human t-PA molecule. Furthermore, the T103N, N117Q t-PA variant retains its reduced clearance as compared to wild-type human t-PA (or Activase® t-PA).

The addition of a further mutation at positions 296–299 of the wild-type human t-PA molecule, that is known to yield a remarkable improvement in fibrin specificity [KHRR(296–299)AAAA], generates a triple mutant which is superior compared to wild-type human t-PA due to its significantly reduced clearance rate and increased fibrin specificity without any significant loss in fibrin binding.

5. In vivo Clot Lysis Assay (Rabbit Arterio-Venous Shunt Thrombolysis Model)

Clots were formed ex-vivo by placing 0.2 ml of either fresh 70% rabbit whole blood (diluted with 0.15M NaCl) or EDTA-collected rabbit platelet rich plasma (0.8×10⁶ platelets/μl) into the barrel of a 0.5 ml syringe. Human thrombin and CaCl₂ were added to the platelet rich plasma (final concentrations of 0.2 μg/ml and 15 mM respectively). Aliquots of whole blood and platelet rich plasma were spiked with I$^{125}$ human fibrinogen prior to transfer to the syringes. A length of cotton thread passed through the syringe barrel, which served to anchor the forming clots. After the clots were incubated at 37° C. for one hour, the plunger was removed and the syringes (1 whole blood and 1 platelet rich) were fitted to silastic tubing. This tubing was attached to catheters that had been previously implanted into a carotid artery and a jugular vein of a 2.5 to 3.0 kg New Zealand White rabbit. Blood passed from the arterial circulation over the clot and returned via the venous side. Blood flow through the shunt was approximately 20 ml/min. Activase® t-PA was administered via the venous catheter as an infusion over 90 minutes (15% loading dose). T103N, N117Q, KHRR(296–299)AAAA was administered as an intravenous bolus. Heparin (300 U/kg) was also administered as a bolus via this route at −10 minutes and 45 minutes. Thrombolysis was monitored by an external gamma detector over the 120 minute time course of the experiment. Relative potency was determined from a semi-log plot of dose response curves for the mutants relative to an Activase® t-PA standard curve. At the completion of one experimental day, the clot circuit was removed and the catheters flushed with saline and locked with heparin (500 units/catheter). Ten animals were used once a day for as many as five consecutive days. The results are shown in FIGS. 3–6.

Figure 4:
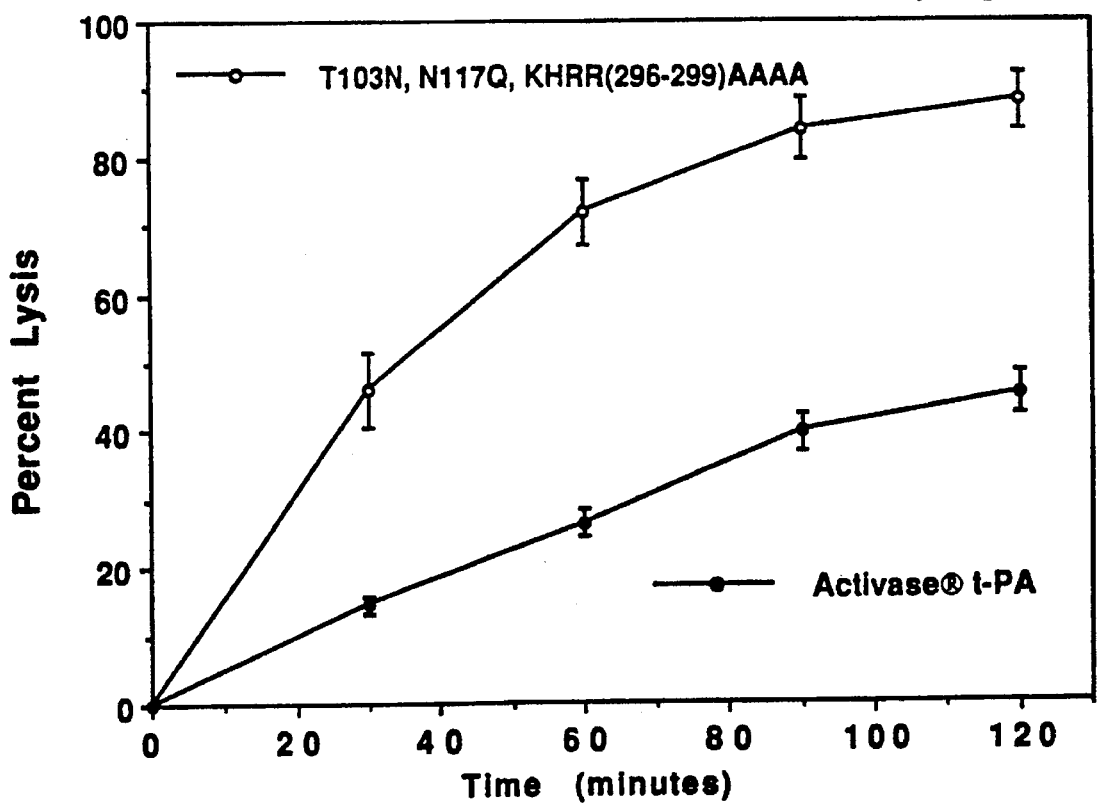
Figure 5:
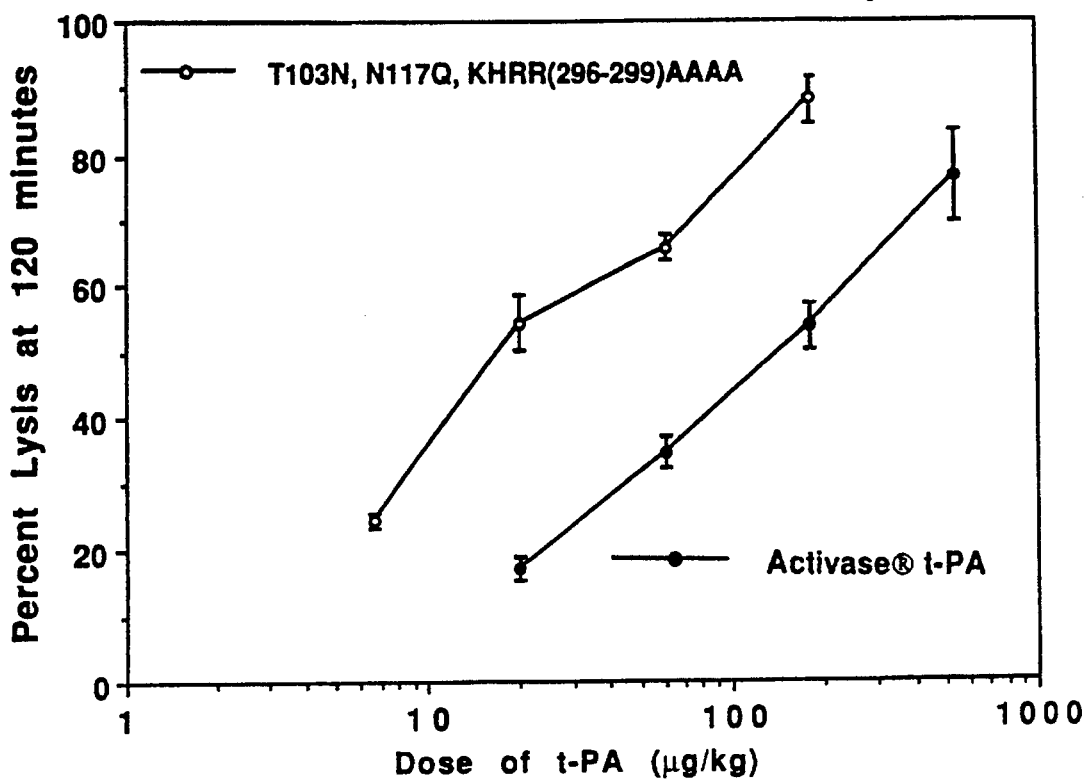
Figure 6:
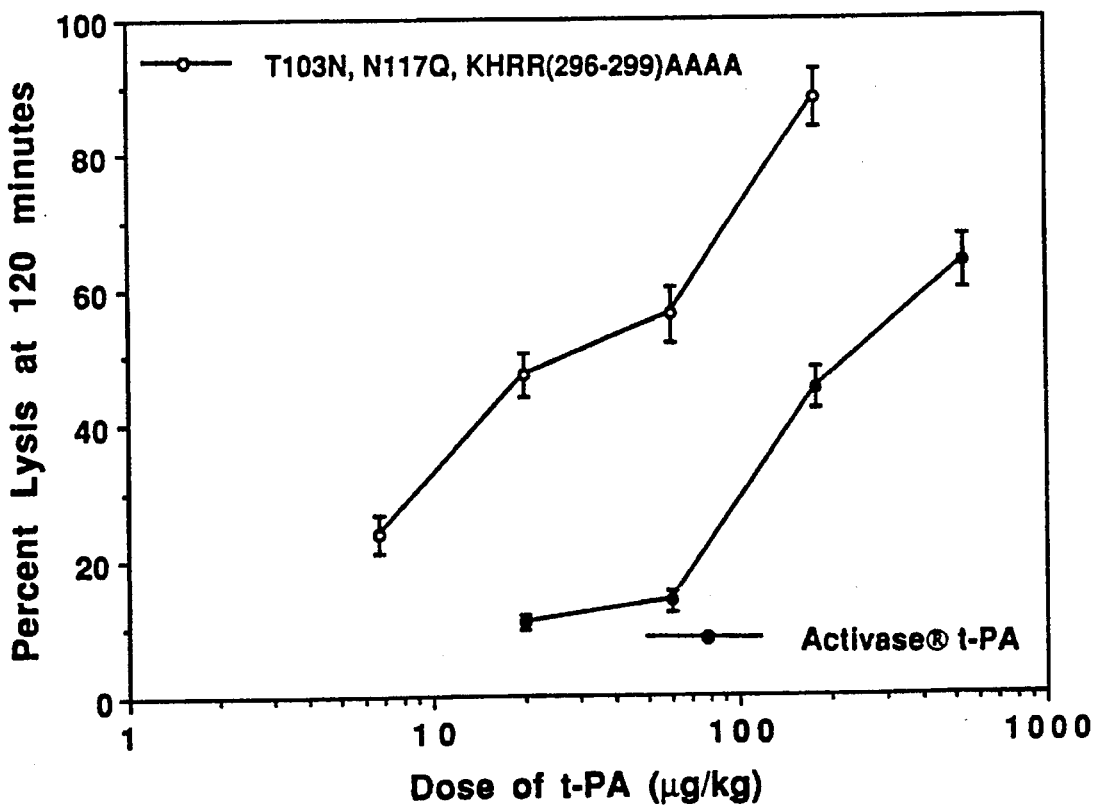

The in vivo data show that clot lysis is achieved with the triple mutant T103N, N117Q, KHRR(296–299)AAAA t-PA significantly more rapidly than with Activase® t-PA both on whole blood clots and on platelet rich clots (FIGS. 3 and 4). The data further show that the in vivo potency of T103N, N117Q, KHRR(296–299)AAAA t-PA is 6.0-fold and 9.5-fold greater than Activase® t-PA on whole blot clots and platelet rich clots, respectively (FIGS. 5 and 6). These numerical data were determined based upon parallel linear curves fitted to the experimental points set forth in FIGS. 5 and 6.

The entire disclosures of all citations cited throughout the specification, and the references cited therein, are hereby expressly incorporated by reference.

Deposit of Materials

E. coli 294 cells transformed with the vector pSVIB5 were deposited with the American Type Culture Collection, 12301 Parklawn Drive, Rockville, Md., USA (ATCC) on 25 Oct. 1989, and were assigned the ATCC Accession No. 68,151. The deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638). All restrictions on the distribution of ATCC 68,151 were removed as of 11 Feb. 1992.

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited. The deposit of material herein does not constitute an admission that the written description herein contained is inadequate to enable the practice of any aspect of the invention, including the best mode thereof, nor is it to be construed as limiting the scope of the claims to the specific illustration that it represents.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

What is claimed is:

1. A method of treating a mammal to prevent fibrin deposition or adhesion formation or reformation comprising administering to a site on the mammal of potential fibrin or adhesion formation an effective amount of a composition comprising a human tissue plasminogen activator (t-PA) variant having an N-linked glycosylation at any of positions 103–105, devoid of functional carbohydrate structure at position 117, and having a substitution, other than the substitution of aspartic acid for arginine at position 299, within the amino acid region 296–302 of the wild-type human t-PA amino acid sequence, said variant exhibiting: a) extended circulatory half-life and substantially retained fibrin binding, or b) improved in vivo fibrinolytic potency, as compared to wild-type human t-PA, in admixture with a pharmaceutically acceptable carrier.

2. The method of claim 1 wherein said human t-PA variant is T103N, N117Q, KHRR(296–299)AAAA t-PA.

* * * * *

UNITED STATES PATENT AND TRADEMARK OFFICE
CERTIFICATE OF CORRECTION

PATENT NO.    :    5,612,029

DATED    :    MARCH 18, 1997

INVENTOR(S)    :    WILLIAM BENNETT, BRUCE KEYT, NICHOLAS PAONI

It is certified that error appears in the above-identified patent and that said Letters Patent is hereby corrected as shown below:

On title page,

Please insert --[*]    Notice:    The term of this patent shall not extend beyond the expiration date of Pat. No. 5,385,732--

Signed and Sealed this

Twelfth Day of August, 1997

Attest:

BRUCE LEHMAN

Attesting Officer    Commissioner of Patents and Trademarks